United States Patent [19]
McNamara et al.

[11] Patent Number: 6,007,996
[45] Date of Patent: Dec. 28, 1999

[54] IN SITU METHOD OF ANALYZING CELLS

[75] Inventors: George McNamara; Dirk Soenksen, both of Carlsbad, Calif.; Dario Cabib, Timrat; Robert A. Buckwald, Ramat Yishay, both of Israel

[73] Assignee: Applied Spectral Imaging Ltd., Migdal Haemek, Israel

[21] Appl. No.: 09/122,704

[22] Filed: Jul. 27, 1998

Related U.S. Application Data

[63] Continuation of application No. 08/571,047, Dec. 12, 1995, Pat. No. 5,784,162.

[51] Int. Cl.$^6$ ............................. C12Q 1/68; G01N 33/53; G06K 9/00
[52] U.S. Cl. ..................................... 435/6; 435/7.1; 382/6
[58] Field of Search ............................. 435/6, 7.1; 382/6, 382/9, 128; 356/346

[56] References Cited

U.S. PATENT DOCUMENTS

| | | | |
|---|---|---|---|
| 4,741,043 | 4/1988 | Bacus | 382/6 |
| 4,998,284 | 3/1991 | Bacus et al. | 382/6 |
| 5,016,283 | 5/1991 | Bacus et al. | 382/6 |
| 5,086,476 | 2/1992 | Bacus | 382/6 |
| 5,134,662 | 7/1992 | Bacus et al. | 382/9 |
| 5,202,931 | 4/1993 | Bacus | 435/7.23 |
| 5,252,487 | 10/1993 | Bacus et al. | 436/8 |
| 5,281,517 | 1/1994 | Bacus et al. | 435/6 |
| 5,288,477 | 2/1994 | Bacus | 424/2 |
| 5,428,690 | 6/1995 | Bacus | 382/128 |
| 5,473,706 | 12/1995 | Bacus et al. | 382/133 |
| 5,526,258 | 6/1996 | Bacus | 364/413.1 |
| 5,539,517 | 7/1996 | Cabib et al. | 382/6 |
| 5,546,323 | 8/1996 | Bacus et al. | 364/497 |

*Primary Examiner*—Eggerton A. Campbell
*Attorney, Agent, or Firm*—Mark M. Friedman

[57] ABSTRACT

A method of in situ analysis of a biological sample comprising the steps of (a) staining the biological sample with N stains of which a first stain is selected from the group consisting of a first immunohistochemical stain, a first histological stain and a first DNA ploidy stain, and a second stain is selected from the group consisting of a second immunohistochemical stain, a second histological stain and a second DNA ploidy stain, with provisions that N is an integer greater than three and further that (i) if the first stain is the first immunohistochemical stain then the second stain is either the second histological stain or the second DNA ploidy stain; (ii) if the first stain is the first histological stain then the second stain is either the second immunohistochemical stain or the second DNA ploidy stain; whereas (iii) if the first stain is the first DNA ploidy stain then the second stain is either the second immunohistochemical stain or the second histological stain; and (b) using a spectral data collection device for collecting spectral data from the biological sample, the spectral data collection device and the N stains are selected such that a spectral component associated with each of the N stains is collectable.

63 Claims, 16 Drawing Sheets

Spectral Color image

Hematoxylin binarized image

DAB binarized image[anti-ER]

AEC binarized image [anti-PR] (no signal)

Classification overlay image.
R: AEC
G: DAB
B: Hematoxylin

FIG. 9A
FIG. 9B
FIG. 9C
FIG. 9D
FIG. 9E
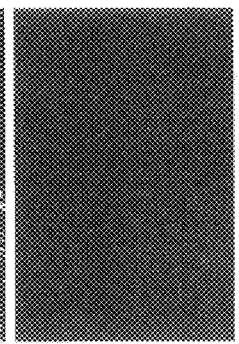
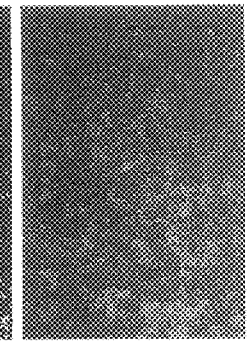
Spectral Color image
Hematoxylin binarized image
DAB binarized image [anti-ER] (no signal)
AEC binarized image [anti-PR]
Classification overlay image.
R: AEC
G: DAB
B: Hematoxylin Spectral Color image Hematoxylin binarized image DAB binarized image [anti-ER] (no signal)

Fast Red binarized image [anti-PR]

Classification overlay image.
R: Fast Red
G: DAB
B: Hematoxylin

Spectral Color image    Hematoxylin binarized image    DAB binarized image [anti-ER]    Fast Red binarized image [anti-PR]    Classification overlay image. R: Fast Red G: DAB B: Hematoxylin FIG. 12A
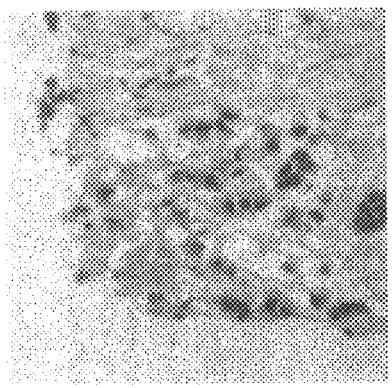
Spectral Color
Blue=Hematoxylin,
Purple=Eosin,
Green=anti-ER
Red=anti-PR
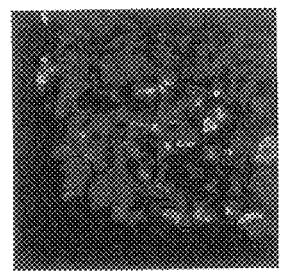
Classification overlay
FIG. 12F
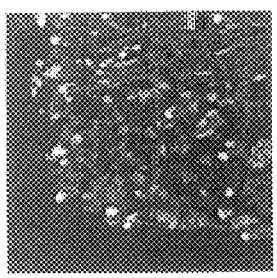
Hematoxylin
FIG. 12B
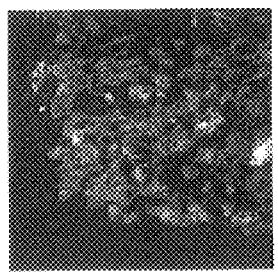
Eosin
FIG. 12C
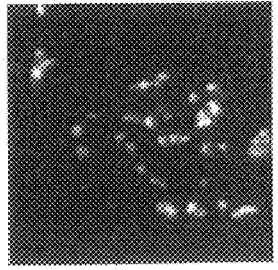
Anti-ER (DAB)
FIG. 12D
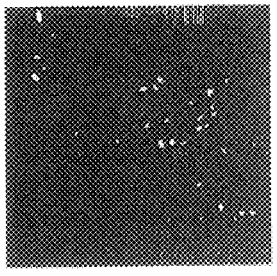
Anti-PR (Fast Red)
FIG. 12E Hematoxylin component image Eosin Y component image Orange G component image Light Green SF component image Spectral Color Image Classification overlay Bismarck Brown Y component image

IN SITU METHOD OF ANALYZING CELLS

This is a continuation of application Ser. No. 08/571,047 filed Dec. 12, 1995, now U.S. Pat. No. 5,784,162.

FIELD AND BACKGROUND OF THE INVENTION

The present invention relates to in situ analysis of cells and, more particularly, to simultaneous in situ analysis of a plurality of immunohistochemical stains, histological stains and/or DNA ploidy stains using spectral imaging techniques, which enable high spatial resolution as well as spectral resolution.

Over the past ten to fifteen years, immunohistochemistry (IHC), which is also known as immunocytochemistry (ICC) when applied to cells, has become an indispensable tool in diagnostic pathology and has virtually revolutionized the practice of surgical pathology. The terms immunohistochemistry and immunocytochemistry are used herein interchangeably. Panels of monoclonal antibodies can be used in the differential diagnosis of undifferentiated neoplasms (e.g., to distinguish lymphomas, carcinomas, and sarcomas); to reveal markers specific for certain tumor types; to diagnose and phenotype malignant lymphomas; and to demonstrate the presence of viral antigens, oncoproteins, hormone receptors, and proliferation-associated nuclear proteins. Not only do such markers have diagnostic significance, but there is a growing body of evidence that some tumor markers have prognostic significance, as has been most extensively demonstrated in breast cancer. These marker studies can be performed by IHC on a variety of specimen types, including cytological preparations, paraffin-embedded tissue, and frozen sections. Most clinical assays employ a single antibody for each slide but by using chromogens of different colors, it is possible to observe/demonstrate two or more markers simultaneously. However, without the use of equipment for processing the appropriate spectral resolution the qualitative or quantitative detection of these chromogens is difficult due to the fact that their absorption coefficients spectrally overlap.

For most applications of IHC, qualitative assessment of the staining patterns is sufficient, because it is the overall staining pattern of the tissue and the cells of interest that imparts the diagnostic information. The human visual system is quite adept at such pattern-recognition tasks, which can be performed quite rapidly, although subjectively. However, the human eye or a CCD camera are not at all adapted at high spectral resolution. However, there are certain markers for which image analysis could play an important role. These include detection of hormone receptors, tumor proliferation markers, oncoproteins, tumor suppressor gene products (e.g., p53), chemotherapy resistance factors, tumor angiogenesis, lymphocyte subset analysis, etc.

The general goal of quantitative IHC (QIHC) is to provide objective measurements of immunostaining reactions. These measurements may be useful in data collection for experimental purposes, but the greatest potential of such measurements lies in exploring their use as aids for determining diagnosis, prognosis, or therapy of human disease, especially cancer. Aside from the mechanics of making such measurements, which will be discussed, a number of issues are related to the peculiarities of IHC which potentially affect how the measurements should be made.

Many of the biological markers detected by IHC do not exhibit a simple "all-or-none" type of expression, and the cellular populations being studied may exhibit considerable heterogeneity with regard to positivity and degree of staining. The localization of the staining reaction may also be important, because some antigens can be expressed on the plasma membrane, in the cytoplasm, or in the cell nucleus. Therefore, both the distribution of the marker among the cell populations and subcellular localization need to be taken into account.

Unlike immunostaining using directly fluoresceinated antibodies, in which the degree of staining is related to ligand concentration in a linear fashion, IHC is in theory nonlinear for two reasons: (i) the enzyme reaction forming the precipitation reaction product is nonlinear, and (ii) a variety of amplification strategies are typically employed, using either bridging or complexing reagents, the goal being to increase the staining sensitivity. The result is that the amount of antigen cannot be directly calculated from the intensity of the immunohistochemical staining. In addition, there may be substantial day-to-day variation in the quality of immunostaining, although automation of the staining procedure may provide more consistency than is usually obtained using manual methods.

Some studies, however, do indicate that under certain conditions it may be possible to establish a linear relationship between ligand concentration and degree of immunohistochemical staining, mostly demonstrated using model systems [van der Ploeg M., Duijndam WAL. Matrix models: Essential tools for microscopic histochemical research. *Histochemistry* 1986; 84:283]. It has been suggested that the biotin-avidin method of staining may be less suitable for this purpose than the peroxidase-antiperoxidase method, because the former suffers from high sensitivity for low concentrations of antigen and poor dynamic range, due to steric hindrance at higher antigen concentrations. Rahier et al. [Rahier J., Stevens M., de Menten Y., Henquin J-C. Determination of antigen concentration in tissue sections by immunodensitometry. *Lab Invest* 1989;61:357–363], studying insulin concentration in rat pancreatic islet cells, were able to show excellent correlation between radioimmunoassay and QIHC using image analysis. They make the important observation that using lower concentrations of antibody is key to the success of the method, because higher concentrations of antibody failed to exhibit a linear relationship with insulin content. They also point out that higher concentrations of antibody should be used when the goal of the measurement is to detect all cells containing the antigen of interest, regardless of level. However, even higher spectral sensitivity is required when working at lower level of antibody, especially if multiple antibodies are to be simultaneously employed.

It is clear that any attempt to quantitate the intensity of immunostaining requires the use of calibration standards, possibly cell lines expressing known levels of antigen or some kind of internal reference. These problems need to be addressed in each application of QIHC.

The approach that has been used most commonly in QIHC relies on the measurement of population statistics, such as the percent of positively stained cells, rather than absolute biochemical concentration of the target molecules. This approach is analogous to that used in clinical flow cytometry, where the proportion of a cell population expressing a given surface marker, rather than the level of expression of that marker, is most commonly measured.

For many of the markers of interest, such an approach makes a great deal of sense biologically. For example, if one is interested in the expression of cell cycle-related markers, it is the proportion of cells expressing that marker, rather than the absolute level of expression, which provides information about the proliferative fraction.

For some markers, such as hormone receptor measurement in breast cancer, the standard methods have provided a biochemical determination expressed as concentration. However, tomurs may exhibit striking heterogeneity with regard to expression of these molecules, and measurements that reflect this heterogeneity may provide information that is more biologically relevant. After all, two tumors may exhibit identical biochemical levels of a given molecule and yet have very different proportions of tumor cells that actually express any level at all. This problem is perhaps best illustrated with regard to estrogen receptor measurement in breast cancer.

The ability to measure immunohistochemical reactions in tissue sections or cytological preparations is highly dependent on the choice of staining and imaging methods. The levels of immunostaining (signal) must be detectable above the background (noise), and should be distinguishable from other cellular or tissue features. In IHC, this is standardly addressed by carefully titering the antibodies (primary and secondary) to maximize the specific staining and minimize the background staining. The tissues are visualized using histological stains (also known as counterstains) having a different color than the chromogen, so that the staining reaction can be easily visualized. For example, immunoperoxidase reactions, which yield a brown reaction product, are typically combined with methyl green or toluidine blue histological stains (counterstains) to provide visual contrast. However, when multiple immunohistochemical stains of different label are used in combination with histological stains and/or DNA ploidy stains it is advantageous to be able to distinguish among the marker stains themselves and to further distinguish between the different stains used for counterstaining or for examination of DNA ploidy, such that each spectral component is identifiable independently of the other spectral components. This cannot be achieved according to any of the methods known in the prior art.

Although some image analysis systems employ true color analysis to measure specific regions of the color spectrum, most imaging systems are based on a gray scale (black and white) light measurements, and depend on optical filters to select specific wavelengths of light for measurement. Combinations of stains that show minimal spectral overlap are presently most useful for QIHC. However, a system with increased spectral resolution will enable the use of highly overlapping dyes.

The CAS 200 System (Cell Analysis Systems, Inc., Lombard, Ill.), employs two video cameras, one coupled with a 500 nm bandpass filter and the other with a 650 nm filter. Tissues are immunostained using the immunoperoxidase method with diaminobenzidine (DAB) as the chromogen (brown reaction product) and methyl green as the tissue (nuclear) counterstain. Images of the nuclei of all of the cells in the field are captured by one camera using the 650 nm filter, while the other camera captures images of the brown reaction product at 500 nm, a wavelength at which DAB is maximally transmitted and methyl green is absorbed. The optical density of the reaction product can be determined by converting the light transmission (gray level) to optical density using a calibrated look-up table, and the relative area of the staining reaction (expressed as a percent of the area stained by methyl green) can be calculated. Simple thresholding methods are used to establish the gray levels for capturing the cell nuclei and for setting the lower limit for detection of DAB, based on a slide stained with control antibody. Combinations other than methyl green and DAB may be used, restricted only by the spectral overlap of the reagents and the availability of suitable filter combinations. This system, however, has an inherent limitation. It can only detect two spectrally non-overlapping spectral components. A system with a higher spectral resolution would enable to simultaneously detect a plurality of spectral components, with higher spectral overlap thereamongst.

No standards have yet been established in the field of QIHC with regard to instrumentation, computer algorithms, staining methodology, or performance characteristics (precision, reproducibility) [Wells W. A., Rainer R. O., Memoli V. A. Equipment, standardization, and applications of image processing. *Am J Clin Pathol* 1993; 99:48–56]. Such standardization has been difficult to achieve in another technically related area, flow cytometry, although there has been progress [Muirhead K. A. Establishment of quality control procedures in clinical flow cytometry. *Ann N Y Acad Sci* 1993; 677:1–20; and National Committee for Clinical Laboratory Standards. *Clinical applications of flow cytometry: Quality assurance and immunophenotyping of peripheral blood lymphocytes; tentative guideline.* Villanova: NCCLS; 1992; NCCLS document H42-T (ISBN 1-56238-15.5–5)]. Standardization issues important for clinical laboratory testing, including the precise antibodies and chromogens to be used, the number of fields and tissue sections to be measured, the units used to report results, quality control materials, and instrument calibration have not yet been resolved for QIHC. As will become apparent to the reader, the present invention provides a giant step towards such standardization.

There is a growing body of evidence that tumor cell proliferation has prognostic significance for a variety of commonly occurring malignancies, including lymphoma [Braylan R. C., Diamond L. W., Powell M. L., Harty-Golder B. Percentage of cells in the S phase of the cell cycle in human lymphoma determined by flow cytometry: Correlation with labeling index and patient survival. *Cytometry* 1980; 1:171–174; and Bauer K. D., Merkel D. E., Winter J. N., et al. Prognostic implications of ploidy and proliferative activity in diffuse large cell lymphomas. *Cancer Res* 1986; 46:3173–3178], breast cancer [Clark G. M., Dressler L. G., Owens M. A., Pounds G., Oldaker T., McGuire W. L. Prediction of relapse or survival in patients with node-negative breast cancer by DNA flow cytometry. *N Engl J Med* 1989; 320:627–633; Silvestrini R., Daidone M. G., Gasparini G. Cell kinetics as a prognostic marker in node-negative breast cancer. *Cancer* 1985; 56:1982–1987; and Sigurdsson H., Baldetorp B., Borg A., et al. Indicators of prognosis in node-negative breast cancer. *N Engl J Med* 1990; 322:1045–1053], and colon cancer [Bauer K. D., Lincoln S. T., Vera-Roman J. M., et al. Prognostic implications of proliferative activity and DNA aneuploidy in colonic adenocarcinomas. *Lab Invest* 1987; 57:329–335]. In some studies, tumor cell proliferation has independent prognostic significance, even if total DNA content analysis ("ploidy") does not [Visscher D. W., Zarbo R. J., Greenawald K. A., Crissman J. D. Prognostic significance of morphological parameters and flow cytometric DNA analysis in carcinoma of the breast. *Pathol Ann* 1990; 25(Part-I): 171–210].

Mitotic counts are generally regarded as a poor and unreliable measure of proliferation; yet they require no special preparative methods.

Uptake of radiolabeled thymidine, or "thymidine labeling index" (TLI) is a well-established method and is considered by many to be the "gold standard" for measuring tumor cell kinetics. Although the TLI provides an accurate assessment of S-phase activity and permits histologic correlation, the method is cumbersome and not easily adapted to the clinical laboratory.

Flow cytometry (FCM) has been used extensively to determine cell cycle activity, primarily by quantitation of the S-phase portion of the DNA content analysis ("ploidy"). This method suffers from a number of serious technical limitations, however. First, it may be difficult to obtain single cell suspensions from solid tumors, and variable numbers of tumor cells may be lost during preparation. Second, the tumor cells are variably diluted by benign normal and inflammatory cells, which can lead to underestimation of the S-phase fraction, particularly for DNA diploid tumors. Third, the complexity of the DNA content analysis ("ploidy"), which consists of a series of overlapping curves, may preclude the accurate use of curve-fitting algorithms to measure the S-phase portion of the histogram. Multicenter studies have shown poor reproducibility for flow-cytometric S-phase fraction, making the practical clinical usefulness of the measurement somewhat doubtful. Another problem associated with cell kinetic measurement by flow cytometry is that only the S-phase fraction is typically determined, whereas a significant proportion of the tumor cell population may reside in the $G_1$ phase of the cell cycle, comprised of cells committed to entering the cycle but not yet synthesizing DNA. Conceivably, two tumors may have identical S-phase fractions but differ significantly in the total fraction of cells in the nonresting state, and thus may exhibit different growth kinetics and response to cycle-dependent chemotherapeutic agents.

For all of these reasons, in situ methods of tumor cell cycle analysis may provide more biologically meaningful information than can be obtained using disaggregated tumor cells [Weinberg I. S. Relative applicability of image analysis and flow cytometry in clinical medicine. In: Bauer K. D., Duque R. E., eds. *Flow cytometry: Principles and applications*. Baltimore: Williams and Wllkins; 1992:359–372; and Weinberg D. S. Proliferation indices in solid tumors. *Adv Pathol Lab Med* 1992;5:163—191]. In addition to guaranteeing that the acquired measurements are made specifically on the tumor cells, in situ methods can allow more widespread sampling of the tumor and determination of tumor cell heterogeneity.

The quantitation of nuclear DNA is increasingly coming into practice in both research and clinical applications.

The measurement of DNA content by either flow or image cytometry is based on the assumptions that the amount of stain represents the amount of DNA and that this amount of stain is correctly measured by the instrument. These assumptions would imply that (i) the DNA labelling procedure (fluorescent dye, chromogenic reaction or staining) is specific (all DNA is labelled and only DNA), stoichiometric (staining intensity changes proportionally to DNA content) and stable (staining intensity does not change with time or repeated measurements); (ii) the instrument used to measure either the light emitted by the fluorescent dye or absorbed by the stain is accurate (giving a result close to the true amount of stain) and reproducible (giving very similar measurements when repeated on the same nucleus), even though not close to the true amount of stain, and linear (giving a result that is perfectly proportional to the amount of stain).

Unfortunately, both the staining procedures and prior art instruments have well-known limitations such that the final measurement is not representative of the absolute amount of DNA actually present in a nucleus.

While stoichiometry can easily be verified by routine controls, the specificity is not accessible because there is no alternative method for the cytometric measurement of DNA content at the individual cell level.

For example, (i) very specific fluorescent dyes bind to either G—C (e.g., mithramycin, chromycin A3) or A—T (e.g., Hoechst, DAPI) DNA base pairs and thus detect the DNA only partially and generate measurements that depend on base pair sequences; (ii) the chromogenic reactions, like Feulgen, involve an acid hydrolysis that removes some DNA fragments as rapidly as they are released from the decondensed chromatin. These reactions thus detect the DNA only partially and provide measurements that depend on the euchromatin versus heterochromatin balance; (iii) the fixative medium may impair or facilitate further hydrolysis, depending on the way they interact with histones.

As far as image cytometry of Feulgen-stained nuclei is concerned, the Beer and Lambert laws do not perfectly apply since (i) the linearity of stain to optical density (OD) is progressively lost as OD runs over 1 unit, which is often the case for heavily stained heterochromatin; (ii) the distribution of the dye is not spatially homogeneous and thus introduces a distributional error that increases as the pixel size increases over from the resolution power of the optics; (iii) the absorption coefficient of a dye varies with the wavelength of light so that the densitometric calculation only applies for monochromatic light. Since they do not deliver enough intensity for visual observation (unless combined with huge arc lamps), monochromators are not used in routine image cytometry, but filter are used whose centre on the maximum absorption is ±10 nm, which usually varies from one system to another.

In addition to the above considerations, the preparation and the prior art instruments employed are optical compromises and are thus responsible for reflection, refraction and diffraction due to the glass slide, mounting medium, lenses and prisms. The light not following the expected geometrical pathways contributes to glare, also called Schwarzchild—Villiger effect, which distorts the ratio between the light beam intensity incident to the nucleus and that emerging from the specimen. Therefore, all the pixel $OD_S$ calculated are slightly erroneous. This error increases as the optical field size increases. The use of a high-quality microscope is thus mandatory to decrease this systematic error of densitometric measurements, which is the most important factor contributing to variations of image cytometry measurements.

Also, video cameras are sensitive to vibrations and electromagnetic fields, image afterglow and saturation-all factors contributing to the distortion of the signal before digitization. At present, charge-coupled device (CCD) cameras undoubtedly provide the most reproducible results as far as densitometry is concerned.

The above limitations all contribute to negative errors that have been extensively investigated. It is thus obvious that the true cell DNA content is not accessible to cytometric measurements. It is therefore astounding that some commercially available image cytometry systems provide measurements expressed in picograms DNA per nucleus, thus adding to the general confusion and, in addition, deliberately misleading the clinicians using such systems.

Provided the staining and measuring procedures are correctly performed and controlled, the quantitation of DNA-specific stains can be interpreted in terms of overall proliferative activity and gross cytogenetic aberrations, thus giving a clear indication as to how to proceed further in investigating those tumour characteristics that are of interest for differential diagnosis and prognosis.

Various stains and chromogenic reagents for quantitative staining of DNA have been recommended in the literature (see Table 1), but finally only one of them has gathered world-wide acceptance for DNA cytophotometry, and this is the reaction named after Feulgen and Rossenbeck, often simply named Feulgen reaction. Strictly speaking, the Feulgen reaction is not a stain but a chromogenic reaction. Terms like Feulgen stain and Feulgen reaction is presently the only staining technique which is stoichiometric for DNA, which means that staining of DNA is both quantitative and specific. All the other methods mentioned in Table 1 are quantitative but not specific for DNA. The success of the Feulgen reaction for quantitative DNA staining is certainly based on this uniqueness.

The Feulgen reaction is a complicated cytohistochemical method which consists of various preparatory steps. Principally, the reaction starts with a procedure called acid hydrolysis: slides with the fixed cytological material are immersed in hydrochloric acid (HCl) which splits off the purine bases adenine and guanine from the DNA molecule, thereby generating aldehyde groups in the purine-free DNA molecule, which is then called apurinic acid (APA). In a second step, the slides are immersed in Schiff's reagent containing a dye which binds covalently to the aldehyde groups. After removal of surplus dye the slides are dehydrated and mounted as usual. In correctly stained material, cell nuclei are stained red-violet, and the cytoplasm and background are unstained. The various steps of the Feulgen reaction become critical when they must be standardized to achieve good reproducibility of staining performance. Therefore, a discussion of the relevant preparatory steps must consider potential sources of error.

TABLE 1

Quantitative DNA stains (+, yes; /, no)

| Staining procedures | Quantitave | Stoichiometric |
|---|---|---|
| Feulgen reaction (basic fuchsin) | + | + |
| Feulgen reaction plus Anionic counterstain | + | + |
| Thionin, Feulgen | + | + |
| Thionin, Feulgen plus Anionic counterstain | + | + |
| Gallocyanin chromalum | + | / |
| Methyl green-pyronin Y | + | |
| Thionin alcoholic | + | / |
| Victoria blue B | + | / |

Routinely, HCl is used for acid hydrolysis, but in principle any acid is suitable. The acid has two effects on the DNA molecules: (i) removal of purine bases, which generates aldehyde groups in the DNA molecules; and (ii) depolymerization of the large APA molecules into smaller fragments. These fragments are partly removed from the cell nuclei by diffusion into the acid solution. Generation of aldehyde groups leads to an increase in nuclear staining intensity, whereas the loss of APA fragments leads to a loss of stainable material from the cell nucleus and thus to a decrease of staining intensity. Thus, we have two counter-current chemical reactions, each following specific and complicated kinetics; the resulting reaction curve is called the hydrolysis profile or the hydrolysis curve.

This hydrolysis profile can be subdivided into four phases: (i) increase of staining intensity; (ii) peak phase with maximum staining intensity; (iii) plateau phase with constant staining intensity; and (iv) decrease in staining intensity.

Phase (i) is characterized by continuous generation of aldehyde groups. The loss of APA fragments is minimal in the beginning, and the amount of stainable material in the cell nucleus increases constantly until phase (ii) is reached. The peak can be so short that it is sometimes hardly visible in hydrolysis profiles. During the plateau phase, (iii), one finds a balance between the continuous generation of aldehyde groups and the loss of APA fragments, and consequently, the staining intensity remains constant over a certain period of time. In phase (iv) the loss of APA fragments outruns the generation of new aldehyde groups, and the staining intensity decreases. After prolonged hydrolysis we find the generation of the maximum number of aldehyde groups, but all APA fragments have been removed from the cell nucleus, and staining intensity is zero.

In practice, it is important to stop acid hydrolysis during phase (iii) where smaller variations of the hydrolysis time have virtually no influence on staining intensity.

The shape of the hydrolysis curve is influenced by several factors, only some of which can be standardized.

Highly condensed DNA is less sensitive to acid hydrolysis than decondensed DNA: phases (i) and (iv) are less steep, and the plateau phase is retarded. DNA compactness, as a biological characteristic of cells, varies between different cell types and in the same cell during the cell cycle. Cell preparation techniques such as specimen sampling and especially fixation of the material may artificially influence DNA compactness and thus acid sensitivity.

A high temperature of the acid bath shortens all four phases. Phase (iii) may be as short as only a few seconds, and a prominent plateau may not be detectable. If hydrolysis is topped in the very steep phases (i) or (iv), even minimal variations of processing time lead to considerable variations in staining. Short hydrolysis profiles with an extremely short peak phase are usually found with so-called hot hydrolysis techniques using an acid bath at 60° C., and frequently it is impossible to stop hydrolysis at the right moment, namely in phase (iii). More frequently, cold hydrolysis with 4–5 mol/l HCl is performed at about 22° C. where under routine conditions the plateau phase has a length of several minutes. Acid hydrolysis is then stopped by a short rinse of the slide in tap water.

Various additives to the acid bath have been recommended in the literature, these should minimize the loss of APA fragments from the cell nucleus. These additives, however, do not play an important role for practical purposes.

Schiff's reagent is a colourless aqueous reagent which contains a dye mixture called basic fuchsin. Basic fuchsin is normally composed of four cationic triarylmehine dyes pararosanilin and its methylated homologues rosanilin, magenta II and new fuchsin. Basic fuchsin of high quality contains a high proportion of pararosanilin. Schiff's reagent is colourless because the relevant dyes are present in their leucoform with sulphite bound to the dye molecules. Coloration of Schiff's reagent (based on basic fuchsin) proves loss of sulphite and deterioration of the solution, which should then be discarded. Various substitutes for basic fuchsin have been recommended, among them the thiazine dye thionin. The advantage of thionin is that it stains cell nuclei blue, a color the cystologists and pathologists are used to when they want to check the slide visually), and cytopllasmic counterstaining with eosin Y or Congo red is easily feasible. Schiff's reagent based on thionin is usually not completely colourless.

After staining with the Schiffs reagent the material is rinsed in dye-free sulphite water. The sulphite removes surplus dye from the cell nuclei and cytoplasm, and only the covalently bound dye molecules stay fixed to the APA molecules within the cell nucleus. The background of the slide should be completely unstained when the Feulgen reaction has been performed correctly.

Acid hydrolysis is the most critical step of the Feulgen reaction. A correctly performed hydrolysis should be stopped in the plateau phase. It is important to have HCl of suitable molar concentration at the right temperature (e.g., 5 mol/l HCl at 22° C. or 4.0 mol/l HCl at 27.5° C.). Acid of suitable molar strength is commercially available or can easily be prepared from concentrated HCl. Frequently, HCl stored in the refrigerator at 4° C. is used immediately without waiting for the acid to warm up; this leads to retardation of the hydrolic reaction, which is often stopped before the plateau phase is reached. The use of temperature-controlled water baths is recommended. Where this is not feasible, scrupulous measurement of the temperature of the acid solution helps to avoid erroneous photometric results.

It is of utmost importance to note that changing the fixative may influence the hydrolysis profile dramatically (by changing chromatin compactness and thus acid sensitivity of the DNA). Changing the fixative means that the hydrolysis curve has to be re-evaluated. Therefore, it seems a good recommendation to stick to one staining protocol which has been established in the relevant laboratory and was found to give reliable and consistent staining results.

The staining procedure itself is uncritical. Staining should be carried out for at least 45 minutes to give the reaction sufficient time to be completed. Schiffs reagent of high and consistent quality is commercially available.

Gallocyanin cromalum (GCA) is a cationic oxadine dye which forms complexes with metals. GCA stains DNA and RNA quantitatively. Thus, it is not specific for DNA. Photometric determination of DNA requires either photometric correction for stained RNA or enzymatic or hydrolytic removal of RNA. The Einarson GCA staining protocol prescribes staining times of up to 48 hours at elevated temperature which makes it impossible to use for routine cytology. A modified GCA was proposed by Husain and Watts with staining times of about 15 minutes.

As compared with Feulgen, GCA after Husain and Watts has the following advantages: (i) no acid bath; (ii) staining time only 15 min; and (iii) gray-blue cell nuclei. The disadvantages are: (i) not specific for DNA; (ii) background staining (due to RNA); and (iii) short shelf-life of the staining solution (about 6 weeks). Specificity of staining can be improved by mild hydrolysis (1 mol/l HCl at 22° C. for 10 minutes) which removes RNA but not DNA. Anionic counterstaining is possible without loss of GCA from the stained DNA.

GCA stains both wet and dry fixed material. Dry fixed slides are significantly less intensely stained. Ethanol 99% (v/v) for 10 minutes on wet fixed material or neutral buffered formaldehyde 3.7% (v/v) for dry fixed material are suitable fixatives. If commercial spray fixatives containing polyethylene glycol (PEG) are used, the PEG film on the slide has to be removed prior to staining by washing the slide for 5 minutes in ethanol 99% (v/v).

Both techniques—the Feulgen reaction and GCA—are equally suitable for cytophotometric determination of DNA. However, they give completely different results when the texture of nuclear chromatin is measured at high optical resolution: acid hydrolysis changes the chromatin structure dramatically, and the chromatin texture of Feulgen-stained cell nuclei is absolutely different from the texture of GCA-stained material.

GCA is all in all less critical than the Feulgen reaction and easier to perform. Nevertheless, the authors prefer the Feulgen reaction due to its substrate specificity and the stability of the staining solution. A careful standardization of the protocol, however, is a prerequisite for consistent staining quality.

A variety of monoclonal antibodies directed against cell cycle-related nuclear antigens are commercially available and may be used for immunohistochemical staining of tissues and cells. The number of publications resulting from studies on human tumors using these antibodies is exponentially increasing.

The antibody most commonly employed is Ki-67, which stains a proliferation-related nuclear antigen in human cells of all lineages [Gerdes J., Schwab U., Lemke H., Stein H. Production of a mouse monoclonal antibody reactive with a human nuclear antigen associated with cell proliferation. *Int J Cancer* 1983;31:13–20; Gerdes J., Lemke H., Baisch H., Wacker H.-H., Schwab U., Stein H. Cell cycle analysis of a cell proliferation-associated human nuclear antigen defined by the monoclonal anKi-67. *J Immunol* 1984;133:1710–1715; and Gerdes J., Li L., Schlueter C., et al. Immunobiochemical and molecular biologic characterization of the cell proliferation-associated nuclear antigen that is defined by monoclonal antibody Ki-67. *Am J Pathol* 1991;138:867–873]. This antibody has the useful property of staining nuclei of cells in $G_1$, S, $G_2$, and M phases of the cell cycle, but not the nuclei of resting ($G_0$ phase) cells. Several studies have demonstrated that the proportion of tumor cell nuclei stained by Ki-67 antibody correlates with tumor grade and other prognostic features for a variety of tumor types, including breast carcinoma, lymphoma, meningioma, glial and astrocytic brain tumors, malignant melanoma, and sarcoma. In non-Hodgkin's lymphoma, Ki-67 staining is associated with working classification grade, and increasing proliferative fraction as measured by Ki-67 staining is associated with a worse prognosis. In breast cancer, Ki-67 staining has been correlated with nuclear grade and lymph node status and several studies have shown the prognostic significance of Ki-67 staining in this type of cancer. The clinical usefulness of Ki-67 antibody had been somewhat limited by the fact that the antigen is preserved in frozen tissue and is lost on standard fixation. However, a monoclonal antibody (MIB 1) has been produced which appears to stain the same antigen as stained by Ki-67, yet which can be used on paraffin sections. Thus, it should be possible to perform large retrospective studies on archival paraffin-embedded tissues to determine the prognostic significance of staining with this antibody. The recently described antibody Ki-S1 appears to have similar staining characteristics as Ki-67 and can be used on paraffin sections. The relative fraction of tumor cell nuclei positive for Ki-S1 staining appears to have prognostic significance in breast cancer.

Other proliferation-associated nuclear markers may prove to have clinical utility. PCNA/cyclin is a 36 kDa nuclear protein present in proliferating cells, and is an accessory protein to DNA polymerase-delta. Flow cytometric studies have demonstrated that two fractions of PCNA/cyclin exist in cell nuclei, the fraction that is insoluble in nonionic detergent being more restricted to the S phase of the cell cycle. Immunohistochemical staining for this protein has been demonstrated in frozen and paraffin-embedded tissues fixed in alcohol or formalin, thus permitting study of archival tissues. However, the staining in tissue sections varies depending on the method of tissue preparation and fixation as well as the clone of antibody used, and the degree of antigen detection appears to be sensitive to the duration of fixation, with long fixation times resulting in antigen loss. It was shown that detection of PCNA in paraffin embedded tissue can be improved using a microwave technique; excellent correlation with flow cytometric S-phase fraction was thereby obtained. Nuclei stained for PCNA/cyclin exhibit varying degrees of positivity, and studies have indicated that the more intensely stained nuclei correspond to S-phase cells. These issues are of course important to the accurate quantitation of antigen expression, regardless of the method used.

Antibodies to alpha DNA polymerase have been applied to tissue sections of normal and malignant tissue, and may find clinical utility. P105 is a nuclear antigen expressed starting at the $G_0/G_1$ phase transition, with increasing expression through M phase. However, attempts to use this antibody in tissue sections have met with variable success, and the antibody may prove to be a more useful tool in flow cytometric studies than in tissue section. There are changes in the level expression of a number of oncoproteins during the cell cycle, but use of these markers in analysing cell cycle activity in solid tumors is doubtful as overexpression is not entirely related. Additional markers are listed hereinunder.

In most immunohistochemical studies using antibodies to proliferation-associated nuclear antigens, staining is measured by estimation or by tedious manual counting. The additional time needed to perform such manual analysis makes routine clinical use unlikely, given the time constraints of a busy pathology practice.

Quantitation of staining for nuclear antigens by image analysis provides the means of attaining the speed, accuracy, and reproducibility of such measurements. The CAS 200 System mentioned hereinabove makes use of two video cameras to view the microscopic image separately through optical filters that capture either all of the ethyl green stained nuclei within the field (650 nm), or the brown reaction product of the immunoperoxidase reaction (500 nm) in the same field. By superimposing maps of the green and brown staining regions, a rapid calculation is made of the percent nuclear area occupied by the immunohistochemical reaction. The threshold for positive staining is established using a slide stained with control antibody. It should be noted that this measurement is not identical to "percent positive nuclei", which would require that individual nuclei be counted and correlated with the staining reaction. Such measurements are more easily made on cytological preparations than on tissue sections, where distinguishing individual nuclei, which are frequently touching or overlapping, may be difficult or impossible. Nuclear area measurements are performed rapidly, and the result is expressed as the cumulative average of all the microscopic fields measured. The intensity of the staining reaction is not taken into account in this measurement, although the threshold for positive staining can be adjusted, for example, to measure only the most intensely stained nuclei rather than all positive nuclei. This system is however highly limited in spectral resolution and therefore has limited applications. It will be appreciated that employing a system enabling similar spatial resolution combined with higher spectral resolution would revolutionize the field of QIHC.

While performing QIHC the selection of fields is important, because tumors can be quite heterogeneous with regard to proliferative activity, and it is uncertain whether the average or greatest proliferative activity is most clinically important. In studying malignant lymphomas, for example, Ki-67 staining was measured using either random field selection (computer generated) or selective measurement of fields judged as having the greatest proliferative fraction. The measurement by random field selection proved to correlate well with the grade of lymphoma as well as flow cytometric S-phase fraction, whereas selecting only the most proliferative areas resulted in the loss of these correlations, with no differences noted among grades. Therefore, in malignant lymphomas, measurement of average proliferative activity over a large number of fields is most likely to be informative. In solid tumors having variable amounts of stroma, it is logical to exclude the stroma and inflammatory cells from the measurements. In a study on the measurement of Ki-67 expression in breast cancer, a relatively weak correlation with flow cytometric S-phase fraction was found, which could be expected given the variable dilution of tumor cells unaccounted for by flow cytometry.

If a statistically reliable measurement of average Ki-67 staining is to be obtained, it is necessary to measure sufficient fields such that the variation of the cumulative percent staining does not vary more than 5% of the mean. Some researchers argue that all such measurements should be expressed as the percentage values +/− the margin of error, which can be calculated on the basis of the sample size. The number of fields will vary depending on the heterogeneity within the tumor, but experience as well as statistical analysis has shown that approximately ten to twenty fields should be sufficient to attain a 95% confidence interval in most cases. However, this average measurement may not be necessarily the most biologically relevant.

It was shown using image analysis for measurement of PCNA/cyclin staining in breast cancer that there are significant differences in the degree of tumor cell proliferation in the central and peripheral portions of the tumor. Comparing the proliferation of the in situ and infiltrating components in individual cases of breast cancer, it was shown that although these components usually exhibit similar degrees of Ki-67 staining, occasional discordances are seen which would affect the classification of the tumor as having a low or high proliferative fraction. Assuming that the infiltrating component is the more biologically relevant with regard to clinical course, it appears that careful attention to histopathology is an important consideration in choosing fields for measurement. In addition, changes in the level and pattern of nuclear expression during progression through the cell cycle have been noted for Ki-67 and PCNA/cyclin. Using image analysis, measurement of raining within a limited range of intensity as well as texture analysis may result in measurements more closely related to specific phases of the cell cycle, such as S phase. However, in any case, image analysis while providing excellent spatial resolution is very limited in spectral resolution, which limitation is addressed by the present invention.

Many cases of breast cancer are responsive to hormonal therapy, and the presence of estrogen receptor associated with tumor cells has been shown to have prognostic importance as well as predictive value in selecting patients for anti-estrogen therapy. The determination of tumor estrogen receptor, most commonly by biochemical techniques, has become standard in the diagnosis and treatment of breast cancer. In general, 60% to 70% of patients with estrogen receptor-positive tumors show a response to hormonal therapy, whereas only 5% of receptor-negative cases respond.

In the United States, biochemical assays for estrogen receptor and progesterone receptor are predominantly used in breast cancer, particularly the dextran-coated charcoal (DCC) method. However, a number of technical problems with the biochemical assay limit its usefulness. First, the widespread use of mammography has resulted in an increasing proportion of resected tumors too small for biochemical analysis, which requires 300 to 500 mg of tissue, and fine-needle aspiration samples similarly cannot be evaluated by conventional methods. In Brigham and Women's Hospital, approximately half of the resected breast tumors are too small for DCC analysis. Second, the lack of morphologic correlation can cause considerable error in the biochemical assay, as intermixed benign breast structures may lead to false-positive results, and excessive tumor dilution by normal and inflammatory cells can lead to false-negative results. Sampling error can be difficult to detect unless frozen sections are performed on the tissue prior to processing, a step not usually performed in most laboratories. Third, the DCC method is very labor-intensive. Therefore, there has been great interest in developing assay methods that circumvent these problems and improve the prognostic and therapeutic usefulness of tumor hormone receptor determination.

The commercial availability of monoclonal antibodies to estrogen receptor (ER) and progesterone receptor (PR) has made possible the visual detection of hormone receptors using standard immunohistochemical methods [Greene G. L., Jensen E. V. Monoclonal antibodies as probes for estrogen redetection and characterization. *J Steroid Biochem* 1982; 16:353–359]. Many studies have reported a good correlation between immunohistochemical determination of ER/PR and the standard biochemical method. Most of these studies have employed semiquantitative methods for analysing the immunohistochemical staining in tissue sections, methods that take into account the heterogeneity expression commonly seen in tumors. For example, the HSCORE used by McCarty and co-workers [McCarty K. S., Szabo E., Flowers J. L., et al. Use of a monoclonal anti-estrogen receptor antibody in the immunohistochemical evaluation of human tumors. *Cancer Res* 1986; 46:(Suppl.):4244s–4248s] is derived from a weighted average of the intensity of staining and the percent positive tumor nuclei, and requires subjective evaluation of staining intensity. Using such a method, the sensitivity and specificity of the antibody method compared to the biochemical assay were 88% and 94%, respectively (85). Other studies have shown similar results.

Most studies report optimal sensitivity using cryostat sections of frozen tissue, but cytocentrifuge preparations, needle aspirates, and paraffin sections have all been tested with good results. Some studies have indicated that the immunohistochemical assay for ER is more predictive clinical response to hormonal therapy than the biochemical assay [Pertschuk L..P., Kim D. S., Nayer K., et al. Immunohistochemical estrogen and progesterone receptor assays in breast cancer with monoclonal antibodies: Histopathologic, demographic, and biochemical correlations and relationship to endocrine response and survival. *Cancer* 1990:66:1663–1670]. This is the strongest argument in favour of the newer method. More recently, some of the large cancer study groups in the United States have permitted the use of immunohistochemical determination of ER in their clinical trials, which will lead to more widespread acceptance of this method.

A serious technical limitation in the use of immunohistochemical ER termination has been the difficulty of objectively analyzing and quantitating the staining reaction. Semiquantitative methods, such as the HSCORE do not provide the reproducibility required among laboratories, and standards for measuring and reporting the staining reaction have not yet been established. The use of image analysis does offer an opportunity to provide such a standard of practice for quantitation of hormone receptors in breast cancer, and the nuclear staining pattern is easily adapted for QIHC, as described above for Ki-67 antigen, however, since it is highly limited in spectral resolution it is not applicable for a multiple markers/counter stains study.

The main features of interest to be measured are the percent tumor cell nuclei stained for ER/PR, as well as the intensity of the staining. Both percent positivity (using total nuclear area) and intensity have been incorporated into a quantitative immunohistochemistry (QIHC) score, and an excellent correlation between QIHC score and biochemical determination of ER has been reported. However, intensity of staining is difficult to standardize and is subject to daily variation in the laboratory. A simpler approach, which was used, is to measure only the percent nuclear area stained, which appears to show linear correlation with biochemical ER measurements less than 200 fmole/mg protein. Using a cut-off of 10% positive nuclear area, one achieves 92% sensitivity and 100% specificity for ER, compared to the DCC method. Sklarew and co-workers [Sklarew R. J., Bodmer S. C., Pertschuk L. P. Comparison of microscopic imaging strategies for evaluating immunohistochemical (PAP) steroid receptor heterogeneity. *Cytometry* 1991; 12:207–220] describe an imaging method for measuring heterogeneity of ER in tissue sections in which nuclear pleomorphism and variations in nuclear area caused by tissue sectioning are taken into account. They believe this method provides superior predictive is value for response to endocrine therapy in breast cancer. Again, based on imaging per se, this method is limited in spectral resolution, and is therefore not applicable in the detection of multiple immunohistochemical marker stains/histological stains/DNA ploidy stains.

It is yet uncertain whether hormone receptors measured by QIHC need to be converted to biochemical values, as treatment decisions are based on whether the tumor is positive or negative, not on absolute value. Indeed, the tumor heterogeneity as reported by QIHC may be of greater clinical relevance than biochemical levels, because the presence of a significant tumor fraction negative for hormone receptor may be predictive of failure to respond to therapy. Also, experience has shown that the majority of cases exhibit either no tumor cells positive for ER, or greater than 50% of the cells positive, with few cases occurring near the cut-off of 10% positivity. Therefore, the continuum of values seen in the biochemical assay may more reflect the variable dilution of tumor cells by benign tissue components than the true biologic range of receptor expression. Studies are needed to compare the clinical response to therapy with different image analytic features in order to provide a standard method for reporting QIHC of hormone receptors.

Tumor sampling is another important issue that needs to be addressed in breast cancer. Not infrequently, the frozen portion of the tumor is not completely representative of the entire tumor. For example, the frozen tissue may contain only intraductal tumor, whereas a focus of invasive cancer is discovered on permanent sections. It is assumed that the biologic features of the invasive tumor are the most clinically relevant, and it cannot be assumed that the in situ and invasive tumor components exhibit identical features. A study was performed using image analysis to compare the invasive and non-invasive components of individual breast cancer cases with regard to hormone receptor expression. Good agreement between these components with regard to both absolute expression of ER (positive, negative) and level of expression of ER (percent nuclear area) was found. Discrepancies were observed, however, with regard to PR expression, and so although sampling may not be an important issue for ER, the same may not be true for PR. It was similarly observed differences between the in situ and invasive components of breast cancer with regard to oncogene expression, as reported by others. Therefore, the heterogeneity of expression for each marker must be established in order to provide guidelines for clinical measurement.

Theoretically, any immunohistochemical reaction that localizes in the cell nucleus, cell cytoplasm, or tissue can be quantitated using image analysis. However, analysis of a plurality of markers simultaneously calls for much higher spectral resolution than is inherently available in imaging systems.

Cell surface and cytoplasmic antigens, particularly the products of oncogenes, are of great clinical interest. For example, Slamon and co-workers [Slamon D. J., Godolphin W., Jones L. A., et al. Studies of the HER-2/neu proto-oncogene in human breast and ovarian cancer. *Science* 1989;235:177–182] have shown that both amplification and overexpression of HER-2/neu oncogene in breast and ovarian cancer correlate with a worsened prognosis. In their study, the intensity of immunostaining correlated well with other measures of gene expression, and the level of expression in ovarian cancer correlated with survival. These authors express the idea that measurement of oncogene products using immunohistochemical methods may have distinct advantages over biochemical methods, and may correlate best with clinical outcome.

Various studies have demonstrated the feasibility of QIHC of oncogene expression. Czerniak et al. [(Czerniak B., Herz F., Wersto R. P., et al. Quantitation of oncogene products by computer-assisted image analysis and flow cytometry. *J Histochem Cytochem* 1990;38:463–466] have demonstrated the use of image analysis to measure cellular expression of several oncogene products expressed in the nucleus, cytoplasm, or cell membrane, and found that the results were similar to those obtained using flow cytometry. Czerniak et al. later used imaging to measure Ha-ras expression in bladder cancer [Czerniak B., Cohen G. L., Etkind P., et al. Concurrent mutations of coding and regulatory sequences of the Ha-ras gene in urinary bladder carcinomas. *J Histochem Cytochem* 1992;23:1199–1204], and were able to correlate increased p21 expression with specific gene mutations. Nuclear oncoproteins may be measured using image analysis in a manner similar to that described for hormone receptors and Ki-67 antigen, and expressed either as percent positive nuclear area or as a value that combines staining intensity with positivity. This approach was used by Figge et al. [Figge J., Bakst G., Weisheit K., Solis O., Ross J. S. Image analysis quantitation of immuno-reactive retinoblastoma protein in human thyroid neoplasms with a streptavidin-biotin-peroxidase staining technique. *Am J Pathol* 199 1; 139:1213–1219] to measure retinoblastoma protein in thyroid tumors. Again, however, imaging analysis cannot provide detection of multiple markers simultaneously, although it is clear that such an ability would render QIHC more suitable for clinical applications.

Because of the problems of controlling daily variations in staining intensity, QIHC may require the use of internal controls and calibration standard Bacus et al. [Bacus S. S., Ruby S. G., Weinberg D. S., Chin D., Oriz R., Bacus J. W. HER-2/neu one expression and proliferation in breast cancers. *Am J Pathol* 1990;137:103–111] used a combination of Feulgen stain (to measure DN content) and immunohistochemical staining for HER-2/neu in order to normalize the oncoprotein measurement to DNA content. Tumor cell lines with known levels of expression of the oncogene were used for calibration, to allow for daily variation in staining intensity. The average concentration oncoprotein could thus be computed on a per cell basis and was expressed as a percent of the level measured in a cell line known to exhibit high levels of overexpression. A threshold for overexpression of HER-2/neu was established on the basis of the low level of expression present in normal tissue. Using this approach, the authors were able to correlate oncogene expression with proliferative fraction growth factor expression and DNA content ("ploidy") in breast cancer Bacus S. S., Chin D., Stern R. K., Ortiz R., Ruby S. G., Weinberg D. S. HER-2/neu one expression, DNA ploidy and proliferation index in breast cancers. *Anal Quant Histol* 1992;14:433–445.

Another example of a cellular protein that may have therapeutic importance is the product of the multiple drug resistance (mdr) gene, P-glycoprotein, a cell surface-associated ATPase that appears to be responsible for one mechanism of non-specific chemotherapy resistance. Grogan et al. [Grogan T., Dalton W., Rybsid J., et al. Optimization of immunohistochemical P-glycoprotein assessment in multidrug-resistant plasma cell myeloma using three antibodies. *Lab Invest* 1991; 63:815–824] have shown a correlation between expression of P-glycoprotein and relapse in multiple myeloma, and have demonstrated the use of image analysis for measuring this protein as detected by IHC. They found that QIHC was more sensitive than Western blot for detecting P-glycoprotein expression. Other markers of therapy resistance, such as glutathione transferase and topoisomerase II, might be similarly studied.

The measurement of tumor markers having prognostic and therapeutic significance is becoming an important part of diagnostic surgical pathology and cytology. Given the small size of many of the tumor samples (biopsies and needle aspirates), it will be necessary to use in situ methods, such as IHC, to detect these tumor markers, combined with measurement analysis if quantitation is needed. As for all laboratory tests, standards of practice and performance must be developed for image analysis to ensure the accuracy and reproducibility of these measurements.

Like immunohistochemical stains, histological stains are routinely used in histopathology has proven useful in cancer evaluation.

Histopathology, which forms the foundation of our knowledge about diseases, is a non-quantitative morphological evaluation using stained histological samples in which the formation of chromatin-stain complexes enhances the shape and structure of cells and subcellular components. The nuclear structure may, in isolation, be viewed as a dynamic reflection of the metabolic state of the nucleus and as a physical correlate of its total content of biochemical constituents. The major nuclear components are DNA, RNA, histone and non-histone proteins, inorganic materials and water. These do change during malignant transformation along with cytoplasmic and functional de-differentiation and increase in the nucleo-cytoplasmic ratio. Studies have proven that alterations in nuclear structure, chromatin pattern and nucleolar size and number are morphologic hallmarks of cancer diagnosis. It was shown that computerized nuclear morphometry (CNM) of individual human breast cancer cells obtained by fine needle aspiration biopsy displayed higher reproducibility of classification than subjective observations with conventional histological preparations. Quantitative estimation of various parameters such as two dimensional estimates of average chromatin area in the nucleus, and the number of central chromatin regions have been shown to correlate with prognosis and differentiation in breast cancer. Mean nucleolar profile area and the largest nucleolar microscopic dimension were found to be of prognostic value in ocular melanomas. In astrocytic gliomas, the relationship between optical density and nuclear profile area was shown to correlate with patient survival.

Histopathological classification uses different staining protocols in order to emphasize cellular structures of tissues and cells. The most common staining procedure used is hematoxylin and eosin (H&E); other procedures are the PAS stain for the demarcation of hydrocarbon moieties, Masson's trichrome stain for extracellular staining of collagen and the Romanowsky-Giemsa stain in hematopathology.

In the classical H&E stain, hematoxylin staining of the nuclei is followed by counter-staining of the cytoplasm and various extracellular materials by eosin; in this process of nuclear staining, hematoxylin is oxidized to the purple dye hematein and is provided with a net positive charge by this metallic salt. The H&E staining technique has remained mostly unchanged for over half a century except for automation of some of the steps. This may be due to the fact that the technique is relatively quick, inexpensive, suitable for most situations, comparatively easy to master and, most important, enables accurate microscopic diagnosis of most of the specimens.

In order to answer specific questions, additional techniques are used such as the PAS and Masson's trichrome stains. In PAS staining, substances containing vicinal glycol groups or their amino or alkylamino derivatives are oxidized by periodic acid to form dialdehydes, which combine with Schiff's reagent to form an insoluble magenta compound. Masson's trichrome staining uses phosphotungstic or phosphomolybdic acid in combination with several anionic dyes such as basic fuchsin, light green and hematoxylin.

Romanowsky-Giemsa staining is used routinely in hematological practice to demonstrate the various hemopoietic cells, both in the normal and in the diseased state. In the process of Romanowsky-Giemsa staining, acidic eosin binds to hemoglobin (in red cells) and eosinophylic granules (in granulocytes), while basic azure binds to chromatin and ribosome-rich cytoplasm. Following this phase, eosin and azure B combine to form a complex yielding the purple element known as the Romanowsky-Giemsa effect. Structures exhibiting this effect show a characteristic absorption band at approximately 550 nm, the so-called Romanowsky band. The Romanowsky-Giemsa technique is also used for the demonstration of various lymphoreticular elements (including mast cells) and microorganisms in paraffin-embedded material.

In the evaluation of infiltrating breast carcinomas, ductal and lobular carcinomas may present similar histological appearances [Azzopardi J. G., Chepick O. F., Hartmann W. H., Jafarey N. A., Lombart-Bosch A., Ozello L. (1982). The World Health Organization histological typing of breast tumors. 2nd ed. Am J Clin Pathol 78:806–816]. Some quantitative histopathological variables have been identified by morphological methods as an aid to the differentiation between ductal and lobular carcinomas [Ladekarl M., and Sorensen F. B. (1993). Quantitative histopathological variables in in situ and invasive ductal carcinoma of the breast. AMPIS 101(12):895–903]. The attempts to grade and to differentiate, or in other words to classify the tumors have been based mainly on nuclear morphology and chromatin structure [Ladekarl M. and Sorensen F. B. (1993). Quantitative histopathological variables in in situ and invasive ductal carcinoma of the breast. AMPIS 101(12):895–903; Cornelisse C. J., de Konig H. R., Moolenaar A. J. (1984). Image and flow cytometric analysis of DNA content in breast cancer; relation to estrogen receptor content and lymph node involvement. Anal Quant Cytol Histol 4:9–18; Stenkvist B., Westman-Naeser S., Holmquist J. (1978). Computerized nuclear morphology as an objective method for characterizing human cancer cell populations. Cancer Res 38:4688–4977; Dawson A. E., Austin R. E., Weinberg D. S. (1991). Nuclear grading of breast carcinoma by image analysis. Classification by multivariate and neural network analysis. Am J Clin Pathol 95:S29–S37]. Morphometric classification of other tumor types, such as but not limited to leukemias, lymphomas, sarcomas and other carcinomas [see, for example, Clarke A. M., Reid W. A. and Jack A. S. (1993) Combined proliferating cell nuclear antigen and morphometric analysis in the diagnosis of cancerous lymphoid infiltrates. J. Clin. Pathol. 46:129–134] are also vastly implemented both in research medical practice.

Nevertheless, as was recently published following an NIH workshop which evaluated the reliability of histopathological diagnosis by the best pathologists in the field of cancer diagnostics, there is a discordance among expert pathologists in the diagnosis of neoplasm. Based on this workshop, it was concluded that histopathological decisionmaking is 100% subjective, regardless of the origin of specimen and that this state of affairs in histopathological diagnosis is not confined to a specific tumor, but is applicable to differential diagnosis in every organ. These conclusions were published in an editorial by A. Bernard Ackerman (1996) entitled "Discordance among expert pathologists in diagnosis of melanocytic neoplasm", in Human pathology 27:1115–1116.

Close to 80% of breast carcinomas are of the ductal type [Aaltomaa S., Lipponen P.: Prognostic factors in breast cancer (reviews). Int J Oncol 1:153, 1992; Toikkanen S. Jensuu H. (1990). Prognostic factors and long-term survival in breast cancer in a defined urban population. APMIS 98:1005–1014]. The differentiation between ductal and lobular carcinomas has proven to be useful for evaluation of patient prognosis and determination of treatment [Ellis I. O., Galea M., Broughton N., Locker A., Blaney R. W. and Elston C. W. (1992). Pathological prognostic factors in breast cancer: II Histological type; relationship with survival in a large study with long term follow-up. Histopathology 20:479–489; Eskelinen M., Lipponen P., Papinaho S., Aaltomaa S., Kosma V. M., Klemi P. (1992). DNA flow cytometry, nuclear morphometry, mitotic indices and steroid receptors as independent prognostic factors in female breast cancer. Int J Cancer 51:555–561; and Toikkanen S., Jensuu H. (1990). Prognostic factors and long-term survival in breast cancer in a defined urban population. APMIS 98:1005–1014]. The tumors have some differences in clinical behavior and in the pattern of metastasis; lobular carcinoma is more multifocal and bilateral than ductal carcinoma

[Azzopardi J. G., Chepick O. F., Hartmann W. H., Jafarey N. A., Lombart-Bosch A., Ozello L. (1982). The World Health Organization histological typing of breast tumors. 2nd ed. *Am J Clin Pathol* 78:806–816], and patient survival expectancy is usually better [DiConstanzo D., Rosen P. P., Gareen I., Franklin S., Lesser M. (1990). Prognosis in infiltrating lobular carcinoma: an analysis of "classical" and variant tumors. Am J Surg Pathol 14:12–23; du Toit R. S., Locker A. P., Ellis I. O., Elston C. W., Nicholson R. I., Robertson J. F. R. (1991). An evaluation of differences in prognosis, recurrence patterns and receptor status between invasive lobular and other invasive carcinomas of the breast. Eur J Surg Oncol 17:251–257]. The two tumor types are morphologically different, cells of infiltrating lobular carcinoma are usually smaller than those of ductal carcinoma, less pleomorphic and have fewer mitotic figures. Infiltrating ductal carcinoma cells have more prominent nucleoli [Azzopardi J. G., Chepick O. F., Hartmann W. H., Jafarey N. A., Lombart-Bosch A., Ozello L. (1982). The World Health Organization histological typing of breast tumors. 2nd ed. Am J Clin Pathol 78:806–816].

Some histological types of intraductal carcinoma have been recognized: comedo, cribriform, micropapillary and solid. All are recognized and classified by specific criteria and subdivided primarily by architectural pattern, cellular pleomorphism, and nuclear hyperchromasia [Page D. L., Anderson T. G. (1987). Diagnostic histopathology of the breast. Edinburgh, Scotland: Churchill Livingstone, 120–157; Lagios M. D. (1990). Duct carcinoma in situ pathology and treatment. Surg Clin North Am 70:853–871; and Lennington W. J., Jensen R. A., Dalton L. W., Page D. L.: Ductal carcinoma in situ of the breast: Heterogeneity of individual lesions. Cancer 73:118–124, 1994]. The survival expectancy for lobular carcinomas is usually better than that of ductal carcinomas [DiConstanzo D., Rosen P. P., Gareen I., Franklin S., Lesser M. (1990). Prognosis in infiltrating lobular carcinoma: an analysis of "classical" and variant tumors. Am J Surg Pathol 14:12–23; du Toit R. S., Locker A. P., Ellis I. O., Elston C. W., Nicholson R. I., Robertson J. F. R. (1991). An evaluation of differences in prognosis, recurrence patterns and receptor status between invasive lobular and other invasive carcinomas of the breast. Eur J Surg Oncol 17:251–257]. Lobular carcinomas are more often bilateral and multifocal [Ladekarl M., Sorensen F. B.: Prognostic, quantitative histopathologic variables in lobular carcinoma of the breast. Cancer 72:2602, 1993] and the pattern of metastasis from the tumors was found to be different. Unfortunately, histological classification of breast carcinomas is subjected to low reproducibility and attempts to classify morphological subtypes of lobular carcinomas with different prognoses, therefore seem futile [Ladekarl M., Sorensen F. B.: Prognostic, quantitative histopathologic variables in lobular carcinoma of the breast. Cancer 72:2602, 1993]. Both lobular and ductal types are now thought to arise from the terminal duct—lobular unit.

Characterization of nuclear features by different techniques is used for determination of diagnosis, treatment and prognosis. Quantitative estimation of various histopathological parameters such as two dimensional estimates of nuclear profile area, nuclear profile densities and mitotic profile numbers have been shown to correlate with differentiation and prognosis. Alterations in nuclear structure are the morphologic hallmark of cancer diagnosis. Nuclear size, shape, chromatin pattern have all been reported to change in breast cancer [Pienta K. J., Coffey D. S.: Correlation of nuclear morphometry with progression of breast cancer. Nuclear Morphometry of breast cancer 2012, 1991].

However, heterogeneity in morphology and biology of tumors belonging to the same classification group has been found to be the most prominent feature of breast cancer [Komitowski D. D. and Janson C. P. (1990). Quantitative features of chromatin structure in the prognosis of breast cancer. Cancer 65:2725–2730].

Among 11 cytological parameters that were examined by de-las-Morenas et al. [de-las-Morenas A., Crespo P., Moroz K. and Donnely M. M. (1995). Cytological diagnosis of ductal versus lobular carcinoma of the breast. Acta Cytol 39(5):865–869] using an automated morphometric system on cytological specimens, chromatic pattern, nuclear size and overall cell size were found to be statistically different between infiltrating lobular and infiltrating ductal carcinoma cell nuclei. Thus, the presence of coarsely granular chromatin, nuclear size of more than 44 $\mu m^2$ and cell size of more than 82 $\mu m^2$, were found to be related to ductal carcinoma.

Ladekarl and Sorensen found that the main three-dimensional nuclear size, the main nuclear profile area and the mitotic index were all significantly larger in ductal than in lobular carcinomas, whereas the main nuclear density index was smaller in ductal carcinoma [Ladekarl M., Sorensen F. B.: Prognostic, quantitative histopathologic variables in lobular carcinoma of the breast. Cancer 72:2602, 1993]. Yu et al. also identified some distinct nuclear features useful in the differentiation of infiltrating ductal and lobular carcinoma [Yu G. H., Sneige N., Kidd L. D., Johnston and Katz R. L. (1995). Image analysis derived morphometric differences in fine needle aspirated of ductal and lobular breast carcinoma. Anal Quant Cytol Histol 17(2):88–92].

Beside in solid tumors, the use of histological stains and immunohistochemical markers is also applicable for diagnosis, prognosis and treatment of various hematological malignancies, an example thereof is chronic lymphocytic leukemia (CLL). The over-accumulation of small, mature-appearing, B-lymphocytes in the peripheral blood is a fundamental hallmark of the chronic lymphocytic leukemia (CLL) diagnosis. A sustained cell count of more than $5 \times 10^3$/liter mature-appearing lymphocytes may suggest the transformation from a normal state to leukemia. The majority of normal lymphocytes and the dominant cellular population of CLL both consist of small cells with dense, clumped nuclear chromatin, which makes the distinction between these lymphocytic populations difficult by conventional light microscopy. Some cases differ in morphological feature from the typical mature, small cell B-CLL: (i) a mixture of small lymphocytes and prolymphocytes (>10% and <55%) designated as CLL/PL, or (ii) CLL mixed with large lymphocytes.

The French-American-British group (FAB) has proposed criteria based on cytochemical and immunological methods in order to establish a clear diagnosis. Immunophenotypic analysis reveals large amounts of surface immunoglobulin (slg) in normal B cells which is only weakly expressed, or undetectable, on B-CLL cells. The CLL cell expresses the pan-B antigens CD19 and CD20 and the activation antigens CD5 and CD23, however it does not express the terminal B-cell differentiation antigens exhibited by plasma cells. B-CLL cells express either kappa or lambda-light chains and the monoclonality is essential to establish the diagnosis. Receptors for mouse red blood cell rosettes (MRBC-R) are detectable on both B-CLL cells and normal B cells, however, the two populations express different patterns of complement receptor, which may serve to distinguish therebetween.

U.S. Pat. No. 5,086,476, to Bacus et al., which is incorporated by reference as if fully set forth herein, teaches an image processing method and apparatus for determining a proliferation index of a cell sample by staining the cells with a chromogen for a proliferation substance and a counterstain for the cell nuclei. The chromogen is activated by an antibody-enzyme conjugate which binds to the proliferation substance to produce a stained cell sample. The stained cell sample is examined with an optical microscope, forming a portion of the apparatus, which produces a magnified cell sample image. The apparatus optically filters the cell sample image and produces a pair of optically enhanced proliferation substance and cell nuclei images. The enhanced images are electronically analyzed to determine the amounts of cell nuclei and proliferation substance appearing in the images, respectively. The amounts are then compared to yield a proliferation index for the portion of the cell sample appearing in the cell sample image.

U.S. Pat. No. 5,109,429 to Bacus et al., which is incorporated by reference as if fully set forth herein, teaches a kit for the quantitation of components in cell nuclei, wherein the kit includes a stain and microscopic slides. Each slide has reference cell objects and a specimen cell area for receipt of specimen cells which are stained simultaneously with the reference cell objects.

U.S. Pat. No. 5,202,931 to Bacus et al., which is incorporated by reference as if fully set forth herein, teaches an image analysis system for the quantitation of nuclear proteins in cell populations. Particularly, the hormonal receptor content of fine needle aspirates of human breast carcinomas are evaluated. Estrogen or progesterone receptors are amplified and visualized in the specimen by a staining technique of the immunoperoxidase type. Monoclonal antibodies specific against the receptor are attached to the receptor sites and are then amplified by a bridging antibody which attaches to the monoclonal antibody and a peroxidase-antiperoxidase complex. A chromogen, diaminobenzidine is combined with the complex and treated with hydrogen peroxide to react with the peroxidase forming an insoluble brown precipitate which marks the receptor sites for optical identification. The specimen is then counterstained with another chromogen, methyl green which is specific to the nucleus of each cell. Two monochromatic filterings optically separate the areas stained by the receptor site optical enhancer and the nuclear area optical enhancer. Measurements of the optical density values of the stained receptor areas yield an intensity value directly related to the quantity of hormonal receptor in the specimen. A comparison of the nuclear area containing hormonal receptor with the total nuclear area yields a percentage value which indicates the distribution of cells throughout of the specimen which contain receptor. These two values for intensity and distribution are then combined to yield a predictive score for an assay. The measured score when compared to an empirically derived reference score is predictive of the prognosis of endocrine therapy.

U.S. Pat. No. 5,281,517 to Bacus et al., which is incorporated by reference as if fully set forth herein, teaches a method and apparatus for selecting and analyzing a subpopulation of cells or cell objects for a certain parameter such as DNA using image analysis means. The cells are first stained with an alkaline phosphatase technique including a monoclonal antibody specific to a protein in at least one of the cell's cytoplasm or on a cell membrane, thereby marking any cells including the protein as to type. A second staining of the DNA in the nucleus is accomplished by a Feulgen technique that destroys the cell cytoplasm. After the staining and marking, the cells may then be gated using the image analysis means on the visual parameter such as colored DNA or colored antigen into a subpopulation that is to be measured. The selected cells may then be examined by digital image processing and measured for a parameter such as a true actual measurement of DNA in picograms. A quantitation of the measured parameter may be generated and provided.

U.S. Pat. No. 5,428,690 to Bacus et al., which is incorporated by reference as if fully set forth herein, teaches an apparatus and method for automated assay of biological specimens positioned on microscope slides. The apparatus comprises an interactive optical subsystem for viewing the biological specimen on the slide and for producing an interactive video signal corresponding to the viewed image. An automated optical subsystem includes a single high power microscope objective for scanning a rack of slides, portions of which having been previously identified for assay in the interactive optical means. The system also includes a processor for processing the interactive and automatic video signals for the two optical subsystems. The processor receives the automatic video signal and performs biological assay functions upon it. A method and apparatus are also disclosed for marking points for later analysis on the microscope slides and for associating an analysis function with each marked point.

U.S. Pat. No. 5,252,487 to Bacus et al., which is incorporated by reference as if fully set forth herein, teaches an apparatus and method for determining an amount of oncogene protein product copies in a cell includes an optical conversion module for measuring an amount of optically enhanced DNA in a cell sample. A subsystem for measuring an amount of an optically enhanced oncogene protein product protein product is coupled to the DNA measuring means. A subsystem for comparing the measured DNA amount and measured oncogene protein product amount produces an oncogene protein product copy measurement which is fed to an output device for producing an output indicative of the amounts of the oncogene protein product in the cells of the cell sample.

U.S. Pat. No. 5,288,477 to Bacus et al., which is incorporated by reference as if fully set forth herein, teaches a method for prognosticating the effectiveness of a chemotherapy using monoclonal antibodies and ligand molecules. The putative anti-cancer agent has binding specificity for a oncogenic receptor molecule on the membrane of a cancer cell, such as HER-2/neu. When the putative agent binds to the oncogenic receptor, the receptor translocates from the membrane to the cytoplasm or perinucleus of the cancer cell, accompanied by a transient increase in the total cellular content of the receptor, and results in terminal cell differentiation. The efficacy of the agent in vivo can be determined in vitro by treatment of biopsied cancer cells with the agent and subsequent examination of the cells for evidence of terminal cell differentiation. Such evidence includes morphological change, reduction in cell growth, or production of chemicals associated with the mature phenotype. Additionally, treated cells may be examined with immunohistochemicals specific for the oncogenic receptor, to determine translocation of the receptor from the membrane to the cytoplasm or perinucleus. Quantification of receptor levels in treated cells by measuring optical densities after staining can be used to determine translocation, as well as a transient increase in total cellular content of the receptor.

U.S. Pat. No. 5,134,662 to Bacus et al., which is incorporated by reference as if fully set forth herein, teaches a method and apparatus for use in performing automated classification of cells and other microscopic specimens. The apparatus provides a compact, adjustable assembly that is operable to provide: an operator-apparatus interactive classification system for the cell analysis; alternative techniques for different cells, cytoplasms and cell populations; and enhanced image or color separation and analysis.

U.S. Pat. No. 5,473,706 to Bacus et al., which is incorporated by reference as if fully set forth herein, teaches an apparatus and method for automated assay of biological specimens positioned on microscope slides. The apparatus comprises an interactive optical subsystem for viewing the biological specimen on the slide and for producing an interactive video signal corresponding to the viewed image. An automated optical subsystem includes a single high power microscope objective for scanning a rack of slides, portions of which having been previously identified for assay in the interactive optical subsystem. The system also includes a processor for processing the interactive and automatic video signals from the two optical subsystems. The processor receives the automatic video signal and performs biological assay functions upon it.

U.S. Pat. No. 5,526,258 to Bacus et al., which is incorporated by reference as if fully set forth herein, teaches an apparatus and method for analyzing the cell objects of a cell sample for the diagnosis and treatment of actual or suspected cancer is disclosed. An image of the cell sample is first digitized and morphological attributes, including area and DNA mass of the cell objects are automatically measured from the digitized image. The measured attributes are compared to ranges of attribute values which are preestablished to select particular cell objects having value in cancer analysis. After the selection of cell objects, the image is displayed to an operator and indicia of selection is displayed with each selected cell object. The operator then reviews the automatically selected cell objects, with the benefit of the measured cell object attribute values and accepts or changes the automatic selection of cell objects. In a preferred embodiment, each selected cell object is assigned to one of six classes and the indicia of selection consists of indicia of the class into which the associated cell object has been placed. The measured DNA mass of identified cell object fragments in tissue section samples may also be increased to represent the DNA mass of the whole cell object from which the fragment was sectioned.

U.S. Pat. No. 5,546,323 to Bacus et al., which is incorporated by reference as if fully set forth herein, teaches an apparatus and method for measuring the thickness of a tissue section with an automated image analysis system, preferably using polyploid nuclear DNA content, for subsequent use in analyzing cell objects of a specimen cell sample for the diagnosis and treatment of actual or suspected cancer or monitoring any variation in the nominal thickness in a microtome setting. An image of a measurement material, such as a rat liver tissue section, having known cell object attributes is first digitized and the morphological attributes, including area and DNA mass of the cell objects, are automatically measured from the digitized image. The measured attributes are compared to ranges of attribute values which are preestablished to select particular cell objects. After the selection of the cell objects, the operator may review the automatically selected cell objects and accept or change the measured cell object attribute values. In a preferred embodiment, each selected cell object is assigned to one of three classes corresponding to diploid, tetraploid and octoploid cell morphology and the measured DNA mass of the identified cell object fragments in the rat liver tissue section sample may be corrected. Next, the selected cell objects of the measurement material, e.g., DNA Mass, are then graphically displayed in a histogram and the thickness of the rat liver tissue section can be measured based upon the distribution.

U.S. Pat. No. 5,018,209 to Bacus et al., which is incorporated by reference as if fully set forth herein, teaches a method and apparatus for selecting and analyzing a subpopulation of cells or cell objects for a certain parameter such as DNA, estrogen, and then measuring the selected cells. The observer in real time views a field of cells and then gates for selection based on the morphological criteria those cells that have the visual parameter such as colored DNA or colored antigen into a subpopulation that is to be measured. The selected cells are examined by digital image processing and are measured for a parameter such as a true actual measurement of DNA in picograms. A quantitation of the measured parameter is generated and provided.

U.S. Pat. No. 4,998,284 to Bacus et al., which is incorporated by reference as if fully set forth herein, teaches a method and apparatus for use in performing automated classification of cells and other microscopic specimens. The apparatus provides a compact, adjustable assembly that is operable to provide: an operator-apparatus interactive classification system for the cell analysis; alternative techniques for different cells, cytoplasms and cell populations; and enhanced image or color separation and analysis.

U.S. Pat. No. 4,741,043 to Bacus et al., which is incorporated by reference as if fully set forth herein, teaches a user interactive system for dynamically testing and evaluating various cells, antigens, or other materials taken from the human body. More specifically, the DNA in specimen cells is analyzed and quantified by image analysis using pattern recognition techniques. The user is provided with a unique slide or support on which there are specimen and reference materials or objects which are simultaneously stained or otherwise image enhanced at the time of analysis.

The following conclusions can be drawn from the above discussion.

First, in situ analysis of neoplasm may be useful for clinical applications, to enable better diagnosis, prognosis and treatment strategy.

Second, histological stains, unique immunohistochemical markers and DNA ploidy stains, both conventional and immunostains, are all useful for that purpose.

Third, so far it was not attempted or suggested to use a plurality of specific immunohistochemical stains combined with several histological stains and DNA ploidy stains to label cells and thereafter extract pathological data therefrom because, while systems providing the adequate spatial resolution (imaging systems) are widely used, systems providing the adequate spatial resolution combined with an adequate spectral resolution are much less abundant.

Such systems, however, were developed and recently were employed for various applications as further detailed hereinunder.

A spectrometer is an apparatus designed to accept light, to separate (disperse) it into its component wavelengths, and measure the lights spectrum, that is the intensity of the light as a function of its wavelength. An imaging spectrometer is a spectrometer which collects incident light from a scene and measures the spectra of each pixel (i.e., picture element) thereof.

Spectroscopy is a well known analytical tool which has been used for decades in science and industry to characterize materials and processes based on the spectral signatures of chemical constituents therein. The physical basis of spectroscopy is the interaction of light with matter. Traditionally, spectroscopy is the measurement of the light intensity emitted, scattered or reflected from or transmitted through a sample, as a function of wavelength, at high spectral resolution, but without any spatial information.

Spectral imaging, on the other hand, is a combination of high resolution spectroscopy and high resolution imaging (i.e., spatial information). Most of the works so far described concern either obtaining high spatial resolution information from a biological sample, yet providing only limited spectral information, for example, when high spatial resolution imaging is performed with one or several discrete band-pass filters [See, Andersson-Engels et al. (1990) Proceedings of SPIE—Bioimaging and Two-Dimensional Spectroscopy, 1205, pp. 179–189], or alternatively, obtaining high spectral resolution (e.g., a full spectrum), yet limited in spatial resolution to a small number of points of the sample or averaged over the whole sample [See for example, U.S. Pat. No. 4,930,516, to Alfano et al.].

Conceptually, a spectral imaging system consists of (i) a measurement system, and (ii) an analysis software. The measurement system includes all of the optics, electronics and the manner in which the sample is illuminated (e.g., light source selection), the mode of measurement (e.g., fluorescence or transmission), as well as the calibration best suited for extracting the desired results from the measurement. The analysis software includes all of the software and mathematical algorithms necessary to analyze and display important results in a meaningful way.

Spectral imaging has been used for decades in the area of remote sensing to provide important insights in the study of Earth and other planets by identifying characteristic spectral absorption features originating therefrom. However, the high cost, size and configuration of remote sensing spectral imaging systems (e.g., Landsat, AVIRIS) has limited their use to air and satellite-born applications [See, Maymon and Neeck (1988) Proceedings of SPIE—Recent Advances in Sensors, Radiometry and Data Processing for Remote Sensing, 924, pp. 10–22; Dozier (1988) Proceedings of SPIE—Recent Advances in Sensors, Radiometry and Data Processing for Remote Sensing, 924, pp. 23–30].

There are three basic types of spectral dispersion methods that might be considered for a spectral bio-imaging system: (i) spectral grating or prism, (ii) spectral filters and (iii) interferometric spectroscopy. As will be described below, the latter is best suited to implement the method of the present invention, yet as will be appreciated by one ordinarily skilled in the art, grating, prism and filters based spectral bio-imaging systems may also be found useful in some applications.

In a grating or prism (i.e., monochromator) based systems, also known as slit-type imaging spectrometers, such as for example the DILOR system: [see, Valisa et al. (September 1995) presentation at the SPIE Conference European Medical Optics Week, BiOS Europe 1995, Barcelona, Spain], only one axis of a CCD (charge coupled device) array detector (the spatial axis) provides real imagery data, while a second (spectral) axis is used for sampling the intensity of the light which is dispersed by the grating or prism as function of wavelength. The system also has a slit in a first focal plane, limiting the field of view at any given time to a line of pixels. Therefore, a full image can only be obtained after scanning the grating (or prism) or the incoming beam in a direction parallel to the spectral axis of the CCD in a method known in the literature as line scanning. The inability to visualize the two-dimensional image before the whole measurement is completed, makes it impossible to choose, prior to making the measurement, a desired region of interest from within the field of view and/or to optimize the system focus, exposure time, etc. Grating and prism based spectral imagers are in use for remote sensing applications, because an airplane (or satellite) flying over the surface of the Earth provides the system with a natural line scanning mechanism.

It should be further noted that slit-type imaging spectrometers have a major disadvantage since most of the pixels of one frame are not measured at any given time, even though the fore-optics of the instrument actually collects incident light from all of them simultaneously. The result is that either a relatively large measurement time is required to obtain the necessary information with a given signal-to-noise ratio, or the signal-to-noise ratio (sensitivity) is substantially reduced for a given measurement time. Furthermore, slit-type spectral imagers require line scanning to collect the necessary information for the whole scene, which may introduce inaccuracies to the results thus obtained.

Filter based spectral dispersion methods can be further categorized into discrete filters and tunable filters. In these types of imaging spectrometers the spectral image is built by filtering the radiation for all the pixels of the scene simultaneously at a different wavelength at a time by inserting in succession narrow band filters in the optical path, or by electronically scanning the bands using acousto-optic tunable filters (AOTF) or liquid-crystal tunable filter (LCTF), see below. Similarly to the slit type imaging spectrometers equipped with a grating or prism as described above, while using filter based spectral dispersion methods, most of the radiation is rejected at any given time. In fact, the measurement of the whole image at a specific wavelength is possible because all the photons outside the instantaneous wavelength being measured are rejected and do not reach the CCD.

Tunable filters, such as AOTFs and LCTFs have no moving parts and can be tuned to any particular wavelength in the spectral range of the device in which they are implemented. One advantage of using tunable filters as a dispersion method for spectral imaging is their random wavelength access; i.e., the ability to measure the intensity of an image at a number of wavelengths, in any desired sequence without the use of filter wheels. However, AOTFs and LCTFs have the disadvantages of (i) limited spectral range (typically, $\lambda_{max}=2\lambda_{min}$) while all other radiation that falls outside of this spectral range must be blocked, (ii) temperature sensitivity, (iii) poor transmission, (iv) polarization sensitivity, and (v) in the case of AOTFs an effect of shifting the image during wavelength scanning, demanding careful and complicated registration procedures thereafter.

All these types of filter and tunable filter based systems have not been used successfully and extensively over the years in spectral imaging for any application, because of their limitations in spectral resolution, low sensitivity, and lack of easy-to-use and sophisticated software algorithms for interpretation and display of the data.

A method and apparatus for spectral analysis of images which have advantages in the above respects was disclosed in U.S. patent application Ser. No. 08/392,019 to Cabib et al., filed Feb. 21, 1995, now U.S. Pat. No. 5,539,517, issued Jul. 23, 1996, which is incorporated by reference as if fully set forth herein, with the objective to provide a method and apparatus for spectral analysis of images which better utilizes all the information available from the collected incident light of the image to substantially decrease the required frame time and/or to substantially increase the signal-to-noise ratio, as compared to the conventional slit- or filter type imaging spectrometer, and does not involve line scanning. According to this invention, there is provided a method of analyzing an optical image of a scene to determine the spectral intensity of each pixel thereof by collecting incident light from the scene; passing the light through an interferometer which outputs modulated light corresponding to a predetermined set of linear combinations of the spectral intensity of the light emitted from each pixel; focusing the light outputted from the interferometer on a detector array, scanning the optical path difference (OPD) generated in the interferometer for all pixels independently and simultaneously and processing the outputs of the detector array (the interferograms of all pixels separately) to determine the spectral intensity of each pixel thereof. This method may be practiced by utilizing various types of interferometers wherein the OPD is varied to build the interferograms by moving the entire interferometer, an element within the interferometer, or the angle of incidence of the incoming radiation. In all of these cases, when the scanner completes one scan of the interferometer, the interferograms for all pixels of the scene are completed.

Apparatuses in accordance with the above features differ from the conventional slit- and filter type imaging spectrometers by utilizing an interferometer as described above, therefore not limiting the collected energy with an aperture or slit or limiting the incoming wavelength with narrow band interference or tunable filters, thereby substantially increasing the total throughput of the system. Thus, interferometer based apparatuses better utilize all the information available from the incident light of the scene to be analyzed, thereby substantially decreasing the measurement time and/or substantially increasing the signal-to-noise ratio (i.e., sensitivity). The sensitivity advantage that interferometric spectroscopy has over the filter and grating or prism methods is known in the art as the multiplex or Fellgett advantage [see, Chamberlain (1979) The principles of interferometric spectroscopy, John Wiley and Sons, pp. 16–18 and p. 263].

Consider, for example, the "whisk broom" design described in John B. Wellman (1987) Imaging Spectrometers for Terrestrial and Planetary Remote Sensing, SPIE Proceedings, Vol. 750, p. 140. Let n be the number of detectors in the linear array, m×m the number of pixels in a frame and T the frame time. The total time spent on each pixel in one frame summed over all the detectors of the array is $nT/m^2$. By using the same size array and the same frame rate in a method according to the invention described in U.S. Pat. No. 5,539,517, the total time spent summed over all the detectors on a particular pixel is the same, $nT/m^2$. However, whereas in the conventional grating or prism method the energy seen by every detector at any time is of the order of 1/n of the total, because the wavelength resolution is 1/n of the range, in a method according to the invention described in U.S. patent application Ser. No. 08/392,019 the energy is of the order of unity, because the modulating function is an oscillating function (e.g., sinusoidal (Michelson) or similar periodic function such as low finesse Airy function with Fabry-Perot) whose average over a large OPD range is 50%. Based on the standard treatment of the Fellgett advantage (or multiplex advantage) described in interferometry textbooks [for example, see, Chamberlain (1979) The principles of interferometric spectroscopy, John Wiley and Sons, pp. 16–18 and p. 263], it is possible to show that devices according to this invention have measurement signal-to-noise ratios which are improved by a factor of $n^{0.5}$ in the cases of noise limitations in which the noise level is independent of signal (system or background noise limited situations) and by the square root of the ratio of the signal at a particular wavelength to the average signal in the spectral range, at wavelengths of a narrow peak in the cases the limitation is due to signal photon noise. Thus, according to the invention described in U.S. Pat. No. 5,539,517, all the required OPDs are scanned simultaneously for all the pixels of the scene in order to obtain all the information required to reconstruct the spectrum, so that the spectral information is collected simultaneously with the imaging information. This invention can be used with many different optical configurations, such as a telescope for remote sensing, a microscope for laboratory analysis, fundus cameras for retinal imaging, fiber optics and endoscopes for industrial monitoring and medical imaging, diagnosis, therapy and others.

In a continuation application (U.S. patent application Ser No. 08/571,047 to Cabib et al., filed Dec. 12, 1995, which is incorporated by reference as if fully set forth herein) the objective was to provide spectral imaging methods for biological research, medical diagnostics and therapy, which methods can be used to detect spatial organization (i.e., distribution) and to quantify cellular and tissue natural constituents, structures, organelles and administered components such as tagging probes (e.g., fluorescent probes) and drugs using light transmission, reflection, scattering and fluorescence emission strategies, with high spatial and spectral resolutions. In U.S. patent application Ser. No. 08/571,047, the use of the spectral imaging apparatus described in U.S. Pat. No. 5,539,517 for interphase fluorescent in situ hybridization of as much as six loci specific probes (each loci located on a different chromosome) was demonstrated, as well as additional biological and medical applications.

Spectral bio-imaging systems are potentially useful in all applications in which subtle spectral differences exist between chemical constituents whose spatial distribution and organization within an image are of interest. The measurement can be carried out using virtually any optical system attached to the system described in U.S. Pat. No. 5,539,517, for example, an upright or inverted microscope, a fluorescence microscope, a macro lens, an endoscope and a fundus camera. Furthermore, any standard experimental method can be used, including light transmission (bright field and dark field), auto-fluorescence and fluorescence of administered probes, etc.

Fluorescence measurements can be made with any standard filter cube (consisting of a barrier filter, excitation filter and a dichroic mirror), or any customized filter cube for special applications, provided that the emission spectra fall within the spectral range of the system sensitivity. Spectral bio-imaging can also be used in conjunction with any standard spatial filtering method such as dark field and phase contrast, and even with polarized light microscopy. The effects on spectral information when using such methods must, of course, be understood to correctly interpret the measured spectral images.

U.S. patent application Ser. No. 08/824,234, filed Mar. 25, 1997, which is incorporated by reference as if fully set forth herein teaches methods for automatic and/or semiautomatic spectrally resolved morphometric classification (e.g., detection, grading) of neoplasm, which are designed to provide objective, as opposed to subjective cell (e.g., cancer cell) classification. According to the method disclosed therein (a) a sample including at least a portion of at least one cell is prepared to be spectrally imaged; (b) the sample is viewed through an optical device optically connected to an imaging spectrometer for obtaining a spectrum of each pixel of the sample; (c) each of the pixels is classified into classification groups according to the pixels spectra; and (d) by analyzing the classification groups of pixels, the cells of the sample are classified into cell classes. This method was exemplified with respect to counterstained breast carcinomas.

The combination of spectral imaging, in situ counterstaining and in situ immunostaining is suggested and attempted herein for the first time. Such a combination enables simultaneous detection of a plurality of immunohistochemical stains, histological stains and DNA ploidy stains which was not possible using the prior art imaging methods. Such a combination is therefore expected to revolutionize the field of cellular pathology by combining data extracted simultaneously from various histological stains, DNA ploidy stains and specific immunohistochemical stains.

There is thus a widely recognized need for, and it would be highly advantageous to have, a method of simultaneous in situ analysis of a plurality of immunohistochemical stains, histological stains and DNA ploidy stains, using spectral imaging techniques of high spatial and spectral resolutions.

SUMMARY OF THE INVENTION

According to the present invention there is provided a method of in situ analysis of a biological sample comprising the steps of (a) staining the biological sample with N stains of which a first stain is selected from the group consisting of a first immunohistochemical stain, a first histological stain and a first DNA ploidy stain, and a second stain is selected from the group consisting of a second immunohistochemical stain, a second histological stain and a second DNA ploidy stain, with provisions that N is an integer greater than three and further that (i) if the first stain is the first immunohistochemical stain then the second stain is either the second histological stain or the second DNA ploidy stain; (ii) if the first stain is the first histological stain then the second stain is either the second immunohistochemical stain or the second DNA ploidy stain; whereas (iii) if the first stain is the first DNA ploidy stain then the second stain is either the second immunohistochemical stain or the second histological stain; and (b) using a spectral data collection device for collecting spectral data from the biological sample, the spectral data collection device and the N stains are selected such that a spectral component associated with each of the N stains is collectable.

According to further features in preferred embodiments of the invention described below, there is provided a method of in situ analysis of a biological sample comprising the steps of (a) staining the biological sample with a plurality of stains of which a first stain is selected from the group consisting of a first immunohistochemical stain, a first histological stain and a first DNA ploidy stain, and a second stain is selected from the group consisting of a second immunohistochemical stain, a second histological stain and a second DNA ploidy stain, with a provision that (i) if the first stain is the first immunohistochemical stain then the second stain is either the second histological stain or the second DNA ploidy stain; (ii) if the first stain is the first histological stain then the second stain is either the second immunohistochemical stain or the second DNA ploidy stain; whereas (iii) if the first stain is the first DNA ploidy stain then the second stain is either the second immunohistochemical stain or the second histological stain; and (b) using a spectral data collection device for collecting spectral data from the biological sample, the spectral data collection device and the plurality of stains are selected such that a spectral component associated with each of the plurality of stains is collectable.

According to still further features in the described preferred embodiments there is provided a method of in situ analysis of a biological sample comprising the steps of (a) staining the biological sample with at least four different immunohistochemical stains; and (b) using a spectral data collection device for collecting spectral data from the biological sample, the spectral data collection device and the at least four immunohistochemical stains are selected such that a spectral component associated with each of the at least four immunohistochemical stains is collectable.

According to still further features in the described preferred embodiments there is provided a method of in situ analysis of a biological sample comprising the steps of (a) staining the biological sample with at least three stains of which at least one stain is an immunohistochemical stain and at least one additional stain is a histological stain or a DNA ploidy stain; and (b) using a spectral data collection device for collecting spectral data from the biological sample, the spectral data collection device and the at least three stains are selected such that a spectral component associated with each of the at least three stains is collectable.

According to still further features in the described preferred embodiments there is provided a method of in situ analysis of a biological sample comprising the steps of (a) staining the biological sample with at least three stains of which a first stain is an immunohistochemical stain, a second stain is a histological stain and a third stain is a DNA ploidy stain; and (b) using a spectral data collection device for collecting spectral data from the biological sample, the spectral data collection device and the at least three stains are selected such that a spectral component specifically associated with each of the at least three stains is collectable.

According to still further features in the described preferred embodiments there is provided an immunohistochemical composition comprising at least four different immunohistochemical stains, each being for staining a respective cytological marker and each being individually detectable in a presence of all others using a spectral data collection device.

According to still further features in the described preferred embodiments the first and second immunohistochemical stains each independently includes a primary antibody and a signal amplification mechanism.

According to still further features in the described preferred embodiments the signal amplification mechanism is selected from the group consisting of a secondary antibody capable of binding a constant region of the primary antibody, avidin or strepavidin capable of binding biotin conjugated to the primary antibody and biotin capable of binding avidin or strepavidin conjugated to the primary antibody.

According to still further features in the described preferred embodiments the secondary antibody, avidin, strepavidin and biotin are each independently labeled with a detectable moiety.

According to still further features in the described preferred embodiments the detectable moiety is a fluorescent dye.

According to still further features in the described preferred embodiments the fluorescent dye is selected from the group consisting of Fluorescein, Rhodamine, Texas Red, Cy2, Cy3, Cy5, Cy0, Cy0.5, Cy1, Cy1.5, Cy3.5, Cy7, VECTOR Red, ELF™ (Enzyme-Labeled Fluorescence), FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1, 3-diazol-4-yl)amino]caproyl] (NBD), BODIPY™, boron dipyrromethene difluoride, Oregon Green, MITOTRACKER™ Red, DiOC$_7$(3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

According to still further features in the described preferred embodiments the detectable moiety is a non-fluorescent dye.

According to still further features in the described preferred embodiments the non-fluorescent dye is selected from the group consisting of alkaline phosphatase, horseradish peroxidase, glucose oxidase and betagalactosidase substrates.

According to still further features in the described preferred embodiments the detectable moiety is an enzyme catalyzing a colorimetric reaction of a substrate having a substantially non-soluble color reaction product.

According to still further features in the described preferred embodiments the enzyme is selected from the group consisting of alkaline phosphatase, horseradish peroxidase, β-galactosidase, and glucose oxidase.

According to still further features in the described preferred embodiments the substrate is selected from the group consisting of alkaline phosphatase, horseradish peroxidase, β-galactosidase, and glucose oxidase substrates.

According to still further features in the described preferred embodiments the detectable moiety is an enzyme catalyzing a luminescence reaction of a substrate having a substantially non-soluble reaction product capable of luminescencing or of directing a second reaction of a second substrate having a luminescencing product.

According to still further features in the described preferred embodiments the enzyme is selected from the group consisting of luciferase and aequorin.

According to still further features in the described preferred embodiments the first and second substrates are each independently selected from the group consisting of luciferine, ATP, $Ca^{++}$ and coelenterazine.

According to still further features in the described preferred embodiments the first and second histological stains are each independently selected from the group consisting of 4',6-diamidino-2-phenylindole, Eosin, Fluorescein isothiocyanate, Hoechst 33258, Hoechst 33342, Propidium Iodide, Quinacrine, Fluorescein-phalloidin, Resorufin, hematoxylin, Orange G, Light Green SF, Romanowsky-Giemsa, May-Grunwald, Blue counterstain, ethyl green, Feulgen-naphthol yellow S, Giemsa, Methylene Blue, Methyl Green, pyronin, Naphthol-yellow, Neutral Red, Papanicolaou stain, Red Counterstain C and Sirius Red.

According to still further features in the described preferred embodiments the first and second DNA ploidy stains are each independently selected from the group consisting of Chromomycin A 3, DAPI, Acriflavine-Feulgen reaction, Auramine O-Feulgen reaction, Ethidium Bromide, Propidium iodide, high affinity DNA fluorophores, Green Fluorescent Protein fused to DNA binding protein, ACMA, Quinacrine and Acridine Orange, Feulgen reagent, Gallocyanin chromalum, Gallocyanin chrom-alum and naphthol yellow S, Methyl green-pyronin Y and Thionin-Feulgen reagent.

According to still further features in the described preferred embodiments the spectral data collection device is selected from the group consisting of an interferometer-based spectral data collection device, filters-based spectral data collection device and a dispersion element-based spectral data collection device.

According to still further features in the described preferred embodiments each of the first and second immunohistochemical stains independently includes a primary antibody.

According to still further features in the described preferred embodiments the primary antibody is selected from the group consisting of anti-estrogen receptor antibody, anti-progesterone receptor antibody, anti-p53 antibody, anti-Her-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

The present invention successfully addresses the shortcomings of the presently known configurations by providing a method of simultaneous in situ analysis of a plurality of immunohistochemical stains, histological stains and DNA ploidy stains, using spectral imaging techniques of high spatial and spectral resolutions.

BRIEF DESCRIPTION OF THE DRAWINGS

The invention herein described, by way of example only, with reference to the accompanying drawings, wherein:

FIGS. 5a–c present hybridization results of 24 chromosomal paints with a normal male chromosome spread using the SPECTRACUBE™ system, wherein FIG. 5a is an RGB image obtained using an RGB algorithm, FIGS. 5b and 5c are classification images obtained using a classification algorithm, whereas FIGS. 5a and 5b present the original spread and FIG. 5c presents the chromosome spread arranged as a karyotype.

FIGS. 8a–e show images of a breast cancer sample which was previously determined to be ER(+)/PR(+) co-stained with the histological stain hematoxylin and with the immunohistochemical stain anti-ER-DAB, wherein FIG. 8a presents an RGB image of the sample, FIGS. 8b–d present binarized images of hematoxylin, DAB and AEC spectral components, respectively, whereas FIG. 8e presents a classification overlay image, wherein the above spectral components are highlighted in red, green and blue, respectively, all as measured using the SPECTRACUBE™ system.

FIGS. 9a–e show images of a breast cancer sample which was previously determined to be ER(+)/PR(+) co-stained with the histological stain hematoxylin and with the immunohistochemical stain anti-PR-AEC, wherein FIG. 9a presents an RGB image of the sample, FIGS. 9b–d present binarized images of hematoxylin, DAB and AEC spectral components, respectively, whereas FIG. 9e presents a classification overlay image, wherein the above spectral components are highlighted in red, green and blue, respectively, all as measured using the SPECTRACUBE™ system.

FIGS. 10a–e show images of a breast cancer sample which was previously determined to be ER(+)/PR(+) co-stained with the histological stain hematoxylin and with the immunohistochemical stain anti-PR-Fast Red, wherein FIG. 10a presents an RGB image of the sample, FIGS. 10b–d present binarized images of hematoxylin, DAB and Fast Red spectral components, respectively, whereas FIG. 10e presents a classification overlay image, wherein the above spectral components are highlighted in red, green and blue, respectively, all as measured using the SPECTRACUBE™ system.

FIGS. 11a–e show images of a breast cancer sample which was previously determined to be ER(+)/PR(+) co-stained with the histological stain hematoxylin and with the immunohistochemical stains anti-ER-DAB and anti-PR-Fast Red, wherein FIG. 11a presents an RGB image of the sample, FIGS. 11b–d present binarized images of hematoxylin, DAB and Fast Red spectral components, respectively, whereas FIG. 11e presents a classification overlay image, wherein the above spectral components are highlighted in red, green and blue, respectively, regions co-stained with anti-ER-DAB and anti-PR-Fast Red are shown in yellow, all as measured using the SPECTRACUBE™ system.

FIGS. 12a–f show images of a breast cancer sample which was previously determined to be ER(+)/PR(+) co-stained with the histological stains hematoxylin and eosin and with the immunohistochemical stains anti-ER-DAB and anti-PR-Fast Red, wherein FIG. 12a presents an RGB image of the sample, FIGS. 12b–e present binarized images of hematoxylin, eosin, DAB and Fast Red spectral components, respectively, whereas FIG. 12f presents a classification overlay image, wherein the above spectral components are highlighted in blue, purple green and red, respectively, all as measured using the SPECTRACUBE™ system.

FIGS. 14a–g show images of a cervix cancer sample co-stained with is the histological stains Harris hematoxylin, eosin, orange G, light green SF and Bismark brown Y, which collectively form what is known in the art as Papanicolaou stain, wherein FIG. 14a presents an RGB image of the sample, FIGS. 14b–f present binarized images of Harris hematoxylin, eosin, orange G, light green SF and Bismark brown Y spectral components, respectively, whereas FIG. 14e presents a classification overlay image, wherein the above spectral components are highlighted in blue, pink, orange, green and gray, respectively, to form by combinations thereof the colorful classification overlay image, all as measured using the SPECTRACUBE™ system.

DESCRIPTION OF THE PREFERRED EMBODIMENTS

Figure 1:
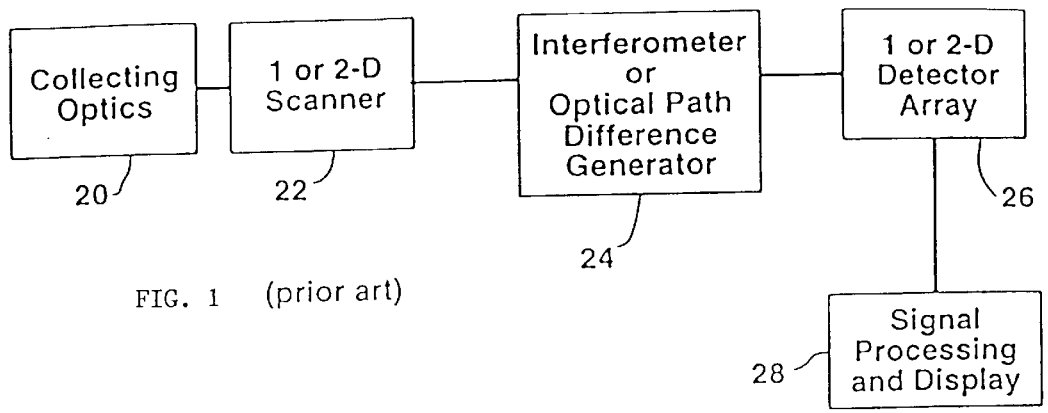
FIG. 1 is a block diagram illustrating the main components of an imaging spectrometer constructed in accordance with U.S. patent application Ser. No. 08/392,019 (prior art).

The present invention is of a method of simultaneous in situ analysis of a plurality of immunohistochemical stains, histological stains and/or DNA ploidy stains which can be used in pathological examination of cells. Specifically, the present invention can be used to provide a pathologist with cumulative information regarding an examined biological sample and assist in decision making.

The principles and operation of a method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Recent studies have shown that the optical mixtures of several absorbing stains can be analyzed in certain cases. Where the absorption bands of the individual stains do no overlap, the analysis is simple and straight forward. Wavelengths are selected where each component in turn displays an absorption adequate for measurement and the other components display negligible absorption. Thus one attenuation measurement at each chosen wavelength suffices to determine each individual stain in the mixture. This technique has been successfully used in pathology specimens by Bacus et al. [ibid.]. The advantages of this technique are that (i) it provides insight into the biochemical composition of the cell or tissue; (ii) image acquisition is simply performed by using narrow band filters. Unfortunately, current cytochemistry and histochemistry offer a very limited number of such dyes with nonoverlapping spectra.

Thus, in accordance with one aspects of the teachings of the present invention there is provided a method of in situ analysis of a biological sample. The method is effected by executing the following method steps, in which, in a first step, the biological sample is stained with N (i.e., a plurality of) stains of which a first stain is a first immunohistochemical stain, a first histological stain or a first DNA ploidy stain, and a second stain is a second immunohistochemical stain, a second histological stain or a second DNA ploidy stain.

Provisions are taken such that N is an integer greater than three (e.g., 4, 5, 6, 7, 8, 9, 10 or more, e.g., an integer between 11 and 50, inclusive) and further that (i) if the first stain is the first immunohistochemical stain then the second stain is either the second histological stain or the second DNA ploidy stain; (ii) if the first stain is the first histological stain then the second stain is either the second immunohistochemical stain or the second DNA ploidy stain; whereas (iii) if the first stain is the first DNA ploidy stain then the second stain is either the second immunohistochemical stain or the second histological stain.

In a second step of the method according to the present invention a spectral data collection device is used for collecting spectral data from the biological sample, the spectral data collection device and the N stains are selected such that a spectral component associated with each of the N stains is collectable.

In accordance with another aspects of the teachings of the present invention there is provided another method of in situ analysis of a biological sample. The method is effected by executing the following method steps, in which, in a first step, the biological sample is stained with at least four different immunohistochemical stains. In a second step of the method a spectral data collection device is used for collecting spectral data from the biological sample, the spectral data collection device and the at least four immunohistochemical stains are selected such that a spectral component associated with each of the at least four immunohistochemical stains is collectable.

In accordance with yet another aspects of the teachings of the present invention there is provided yet another method of in situ analysis of a biological sample. The method is effected by executing the following method steps, in which, in a first step, the biological sample is stained with at least three stains of which at least one stain is an immunohistochemical stain and at least one additional stain is a histological stain or a DNA ploidy stain. In a second step of the method, a spectral data collection device is used for collecting spectral data from the biological sample, the spectral data collection device and the at least three stains are selected such that a spectral component associated with each of the at least three stains is collectable.

In accordance with still another aspects of the teachings of the present invention there is provided still another method of in situ analysis of a biological sample. The method is effected by executing the following method steps, in which, in a first step, the biological sample is stained with at least three stains of which a first stain is an immunohistochemical stain, a second stain is a histological stain and a third stain is a DNA ploidy stain. In a second step of the method, a spectral data collection device is used for collecting spectral data from the biological sample, the spectral data collection device and the at least three stains are selected such that a spectral component specifically associated with each of the at least three stains is collectable.

In accordance with an additional aspects of the teachings of the present invention there is provided a immunohistochemical composition which includes in a mixture at least four different immunohistochemical stains, each being for staining a respective cytological marker in the biological sample and each being individually detectable in a presence of all others using a spectral data collection device.

As used herein in the specification and in the claims section below, the term "in situ" or "in situ analysis" refers to an analysis of cellular or tissue components situated and preferably fixated in their natural place or position within the cell or tissue.

As used herein in the specification and in the claims section below, the term "biological sample" refers to a sample retrieved from an animal, mammals and human beings in particular. The sample may be of a healthy tissue, disease tissue or tissue suspected of being disease tissue. The sample may be a biopsy taken, for example, during a surgical procedure. The sample may be collected via means of fine needle aspiration, scraping or washing a cavity to collects cells or tissue therefrom. The sample may be of a tumor both solid and hematopoietic tumors, as well as of neighboring healthy tissue. The sample may be a smear of individual cells or a tissue section.

As used herein in the specification and in the claims section below, the term "stained" or "staining" refers to a process in which coloration is produced by foreign matter having penetrated into and/or interacted with the biological sample.

As used herein in the specification and in the claims section below, the term "stain" or "stains" refers to colorants, either fluorescent, luminescent and/or non-fluorescent and further to reagents or matter used for effecting coloration.

As used herein in the specification and in the claims section below, the term "immunohistochemical stain" refers to colorants, reactions and associated reagents in which a primary antibody which binds a cytological marker is used to directly or indirectly (via "sandwich" reagents and/or an enzymatic reaction) stain the biological sample examined. Immunohistochemical stains are in many cases referred to in the scientific literature as immunostains, immunocytostains, immunohistopathological stains, etc.

As used herein in the specification and in the claims section below, the term "antibody" refers to any monoclonal or polyclonal immunoglobulin, or a fragment of an immunoglobin such as sFv (single chain antigen binding protein), Fab1 or Fab2.

As used herein in the specification and in the claims section below, the term "histological stain" refers to any colorant, reaction and/or associated reagents used to stain cells and tissues in association with cell components such as types of proteins (acidic, basic), DNA, RNA, lipids, cytoplasm components, nuclear components, membrane components, etc. Histological stains are in many cases referred to as counterstains, cytological stains, histopathological stains, etc.

As used herein in the specification and in the claims section below, the term "DNA ploidy stain" refers to stains which stoichiometrically bind to chromosome components, such as, but not limited to, DNA or histones. When an antibody is involved, such as anti-histone antibody, such stains are also known as DNA immunoploidy stains.

As used herein in the specification and in the claims section below, the term "spectral data collection device" refers to any device capable of detecting light intensity associated with a plurality, typically four or more, of distinct spectral bands in each spatial element (pixel) of the examined sample. For example, the SPECTRACUBE™ system optically connected to a microscope preferably serves as the spectral data collection device according to the present invention. However, any spectral imager, i.e., an instrument that measures and stores in memory for later retrieval and analysis the spectrum of light emitted by every point of an object which is placed in its field of view, including filters (e.g., conventional, acousto-optic tunable filter (AOTF) or liquid-crystal tunable filter (LCTF)) and dispersive element (e.g., grating or prism) based spectral imagers, or other spectral data or multi-band light collection devices (e.g., a device in accordance with the disclosure in Speicher R. M., Ballard S. G. and Ward C. D. (1996) Karyotyping human chromosomes by combinatorial multi-fluor FISH. Nature Genetics, 12:368–375) can be used to acquire the required spectral data. Also a device which includes a plurality of wide band filters (fixed or tunable), as described in U.S. patent application Ser. No. 08/917,213, filed Aug. 25, 1997, and is incorporated by reference as if fully set forth herein, can be used as the spectral data collection device according to the present invention. Therefore, it is intended not to limit the scope of the present invention for use of any specific type of spectral data collection device, nor to any specific type of spectral imager.

Thus, the spectral data collection device can be an interferometer-based spectral data collection device, filter(s)-based spectral data collection device and a dispersion element-based spectral data collection device.

As used herein in the specification and in the claims section below, the term "spectral component" refers to a part of a spectrum which is unique to a specific substance and therefore may be used as a spectral signature of that substance, to differentiate that substance from other substances.

According to one embodiment of the present invention the immunohistochemical stains each independently includes a primary antibody and a signal amplification mechanism. The signal amplification mechanism can employ, for example, a secondary antibody capable of binding a constant region of the primary antibody, avidin or strepavidin capable of binding biotin conjugated to the primary antibody, and biotin capable of binding avidin or strepavidin conjugated to the primary antibody.

According to a preferred embodiment of the present invention, the secondary antibody, avidin, strepavidin or biotin are each independently labeled with a detectable moiety, which can be an enzyme directing a colorimetric reaction of a substrate having a substantially non-soluble color reaction product, a fluorescent dye (stain), a luminescent dye or a non-fluorescent dye. Examples concerning each of these options are listed hereinbelow.

The enzyme employed can be, for example, alkaline phosphatase, horseradish peroxidase, β-galactosidase and/or glucose oxidase; and the substrate can respectively be an alkaline phosphatase, horseradish peroxidase, β-galactosidase or glucose oxidase substrate.

The enzyme can also be directed at catalyzing a luminescence reaction of a substrate, such as, but not limited to, luciferase and aequorin, having a substantially non-soluble reaction product capable of luminescencing or of directing a second reaction of a second substrate, such as but not limited to, luciferine and ATP or coelenterazine and $Ca^{++}$, having a luminescencing product.

Examples for optional histological and DNA ploidy stains which can be employed while implementing the methods of the present invention are given hereinunder.

According to a most preferred embodiment of the present invention each of the immunohistochemical stains employed includes a primary antibody.

According to yet another preferred embodiment of the present invention external calibration is employed to account for day-to-day variations experienced when staining is attempted. Thus, at least one calibration is preferably attempted for every staining batch. To this end, calibration material is employed, wherein the biological sample and the calibration material are stained at the same time with the same staining solutions. The spectral data collection device is first used to analyze the stained calibration material such that adjustment thereof or extraction of calibrating data for algorithmic post measurement calibration becomes feasible. Only then the biological sample can be more meaningfully analyzed, taking into account a calibration based correction. One ordinarily skilled in the art would know how to devise a calibrating algorithm to compensate for day-to-day variations experienced when staining is attempted.

The calibration material can be an optical density reference material. Alternatively, the calibration material can include control cells which are simultaneously co-stained' together with the examined biological sample.

The following lists various dyes or stains which can be used to implement the methods of the present invention. Further included is a list of natural cell constituents having a detectable spectral signature which can be co-detected with the stains using the methods of the present invention.

It will be appreciated by one ordinarily skilled in the art that some staining procedures may interfere with others. Therefore the type of stains employed and their sequence of application should be well considered. These considerations can be applied by one ordinarily skilled in the art, knowing the staining procedures.

Immunohistochemical stains for use in transmittance microscopy: In principle, any enzyme that (i) can be conjugated to or bind indirectly to (e.g., via conjugated avidin, strepavidin, biotin, secondary antibody) a primary antibody, and (ii) uses a soluble substrate to provide an insoluble product (precipitate) could be used. Such enzymes include, for example, HRP, AP, LacZ and glucose oxidase.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/ iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color), Horseradish Peroxidase (HRP, sometimes abbreviated PO) substrates include, but are not limited to, 2,2' Azino-di-3-ethylbenz-thiazoline sulfonate (ABTS, green, water soluble), aminoethyl carbazole, 3-amino, 9-ethylcarbazole AEC (3A9EC, red). Alpha-naphthol pyronin (red), 4-chloro- 1-naphthol (4C1N, blue, blue-black), 3,3'-diaminobenzidine tetrahydrochloride (DAB, brown), ortho-dianisidine (green), o-phenylene diamine (OPD, brown, water soluble), TACS Blue (blue), TACS Red (red), 3,3',5,5' Tetramethylbenzidine (TMB, green or green/blue), TRUE BLUE™ (blue), VECTOR™ VIP (purple), VECTOR™ SG (smoky blue-gray), and Zymed Blue HRP substrate (vivid blue).

Glucose Oxidase (GO) substrates, include, but are not limited to, nitroblue tetrazolium (NBT, purple precipitate), tetranitroblue tetrazolium (TNBT, black precipitate), 2-(4-iodophenyl)-5-(4-nitorphenyl)-3-phenyltetrazolium chloride (INT, red or orange precipitate), Tetrazolium blue (blue), Nitrotetrazolium violet (violet), and 3-(4,5-dimethylthiazol-2-yl)-2,5-diphenyltetrazolium bromide (MTT, purple). All tetrazolium substrates require glucose as a co-substrate. The glucose gets oxidized and the tetrazolium salt gets reduced and forms an insoluble formazan which forms the color precipitate.

Beta-Galactosidase substrates, include, but are not limited to, 5-bromo-4-chloro-3-indoyl beta-D-galactopyranoside (X-gal, blue precipitate).

The precipitates associated with each of the substrates listed have unique detectable spectral signatures (components).

Antibody which links heavy metals can be used for immunostaining using reflection contrast, bright-field or dark-field imaging, or electron microscopy. Such heavy metals include, but are not limited to, gold and silver, typically in a colloidal form.

The following references, which are incorporated herein provide additional examples. J. M. Elias (1990) Immunohistopathology: A practical approach to diagnosis. ASCP Press (American Society of Clinical Pathologists), Chicago; J. F. McGinty, F. E. Bloom (1983) Double immunostaining reveals distinctions among opioid peptidergic neurons in the medial basal hypothalamus. Brain Res. 278: 145–153; and T. Jowett (1997) Tissue In situ Hybridization: Methods in Animal Development. John Wiley & Sons, Inc., New York; J Histochem Cytochem 1997 December 45(12):1629–1641.

Histological stains for use in transmittance microscopy: The following lists some histological stains used in transmitted light microscopy: eosin, hematoxylin, Orange G, Light Green SF, Romanowsky-Giemsa, May-Grunwald, Blue counterstain (Trevigen), ethyl green (CAS), Feulgen-naphthol yellow S, Giemsa, Methylene Blue, Methyl Green, pyronin, Naphthol-yellow, Neutral Red, Papanicolaou stain (which typically includes a mixture of Hematoxylin, Eosin Y, Light Green SF, Orange G and Bismarck Brown, Red Counterstain B (Trevigen), Red Counterstain C (Trevigen), and Sirius Red.

DNA ploidy stains for use in transmittance microscopy: The following lists some DNA ploidy stains used in transmitted light microscopy. Feulgen reagent (pararosanilin), Gallocyanin chrom-alum, Gallocyanin chrom-alum and naphthol yellow S, Methyl green-pyronin Y, Thionin-Feulgen reagent, Immunohistochemical stains for use in fluorescence microscopy: Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1, 3-diazol-4-yl)amino]caproyl] (NBD), BODIPY™, boron dipyrromethene difluoride, Oregon Green, MITOTRACKER™ Red, $DiOC_7(3)$, $DiIC_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

Histological stains for use in fluorescence microscopy: 4',6-diamidino-2-phenylindole (DAPI), Eosin, Fluorescein isothiocyanate (FITC), Hoechst 33258 and Hoechst 33342 (two bisbenzimides), Propidium Iodide, Quinacrine, Fluorescein-phalloidin and Resorufin, DNA ploidy stains for use in fluorescence microscopy: Chromomycin A 3, DAPI, Acriflavine-Feulgen reaction, Auramine O-Feulgen reaction, Ethidium Bromide, Propidium iodide, high affinity DNA fluorophores such as POPO, BOBO, YOYO and TOTO and others, Green Fluorescent Protein fused to DNA binding protein, such as histones, ACMA, Quinacrine and Acridine Orange.

Endogenous pigments: Hemoglobin, myoglobin, porphyrin, hemosiderin and other ferrous pigments, lipofuscin, melanin, neuromelanin, ceroid a fluorescent oxidation product of lipid/protein, carotenoids, pyridine, flavin nucleotides.

The following lists some primary antibodies known to specifically bind their associated cytological markers and which are presently employed as components in immunohistochemical stains used for research and, in limited cases, for diagnosis of various diseases. Anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti- E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oncoprotein (p21) antibody, anti-Lewis X (also called CD15) antibody, anti-Ki-67 antibody (cellular proliferation), anti-PCNA (multiple cancers) antibody, anti-CD3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (Alzheimer's disease), anti-fibrin antibody (epithelial cells), anti-keratins antibody, and anti-Tn-antigen antibody (colon carcinoma, adenocarcinomas, and pancreatic cancer).

Table 2 below provides few examples of sets of markers having prognostic and/or therapeutic significance in various cancers:

TABLE 2

| Cancer | DNA Ploidy | ER | PR | p53 | her-2/ neu | Ki-67 | p21 ras | pRB | CD31 |
|---|---|---|---|---|---|---|---|---|---|
| Breast | X | X | X | X | X | X | | | X |
| Ovarian | X | | | X | X | X | | | X |
| Bladder | X | | | X | | X | | X | X |
| Colorectal | X | | | X | | X | X | | X |
| Prostate/ Bladder | X | | | X | | X | | X | X |

A breast cancer panel therefore can include the anti-ER, anti-PR, anti-Her2/neu, anti-p53, anti-Ki-67 and anti-CD31 immunohistochemical marker stains, a DNA ploidy stain and a H&E counterstain.

Ovarian and/or endometrial cancer panel can therefore include the anti-Her2/neu, anti-p53, anti-Ki-67 and anti-CD31 immunohistochemical stains, a DNA ploidy stain and a H&E counterstain.

Prostate and/or bladder cancer panel can therefore include the anti-Ki-67, anti-p53, anti-CD31 and anti-retinoblastoma protein (Rb) marker stains, a DNA ploidy stain and a H&E counterstain.

Whereas a colorectal cancer panel can therefore include the anti-Ki-67, anti-p53, anti-CD31 and anti-p21 (ras oncoprotein) marker stains, a DNA ploidy stain and a H&E counterstain.

The present invention as herein described has several advantages over prior art methods in which high resolution imaging was combined with very low and inefficient spectral resolution (typically two discrete spectral bands) for co-detection of two stains, because using a spectra collection device as herein described, characterized by high spatial and spectral resolutions enables to co-detect any desired numbers of stains even when the stains employed are very similar spectrally.

Thus according to the present invention a clinician can simultaneously detect multiple cytological markers with prognostic/therapeutic significance (e.g.; ER, PR, p53, her-2/neu, Ki-67 and CD31), significant changes in DNA ploidy and in sample staining with conventional histological stains. The clinician can therefore manage and monitor patient therapy with improved accuracy (e.g., select appropriate therapeutic regimen), reduce patient management costs through more accurate diagnosis, and reduce hospital costs through more efficient sampling.

Scanning fields of the stained biological sample according to the present invention can be effected manually, semi-automatically or automatically, as well known in the art, using for example slide loading and scanning devices. For complete DNA ploidy analysis typical 200 cells, preferably more, should be analyzed. Pattern recognition and spectrally resolved pattern recognition approaches can be used to enhance analysis and diagnosis.

There present invention, according to which a method is provided of simultaneous in situ analysis of a plurality of immunohistochemical stains, histological stains and DNA ploidy stains, using spectral imaging techniques of high spatial and spectral resolutions has numerous advantages over the prior art. First it enables simultaneous detection of a plurality of stains and therefore it is effort and cost-effective. Second, it enables the simultaneous detection of a plurality of stains on the same cells or tissue, while according to the prior art, these is not applicable for more than two or three stains. Third, it enabled dissociating among very similar spectra, while the prior art required the use of very distinctive stains.

EXAMPLES

Reference is now made to the following examples, which together with the above descriptions, illustrate the invention in a non limiting fashion.

Example 1

The Measurement Apparatus and its Performances

FIG. 1 is a block diagram illustrating the main components of a prior art imaging spectrometer disclosed in U.S. patent application Ser. No. 08/392,019 to Cabib et al., filed Feb. 21, 1995, now U.S. Pat. No. 5,539,517, issued Jul. 23, 1996, which is incorporated by reference as if fully set forth herein.

This imaging spectrometer is constructed highly suitable to implement the method of the present invention as it has high spectral (Ca. 4–14 nm depending on wavelength) and spatial (Ca. 30/M $\mu$M where M is the effective microscope or fore optics magnification) resolutions.

Thus, the prior art imaging spectrometer of FIG. 1 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517 alternative types of interferometers may be employed. These include (i) a moving type interferometer in which the OPD is varied to modulate the light, namely, a Fabry-Perot interferometer with scanned thickness; (ii) a Michelson type interferometer which includes a beamsplitter receiving the beam from an optical collection system and a scanner, and splitting the beam into two paths; (iii) a Sagnac interferometer optionally combined with other optical means in which interferometer the OPD varies with the angle of incidence of the incoming radiation, such as the four-mirror plus beamsplitter interferometer as further described in the cited U.S. patent (see FIG. 14 there).

Figure 2:
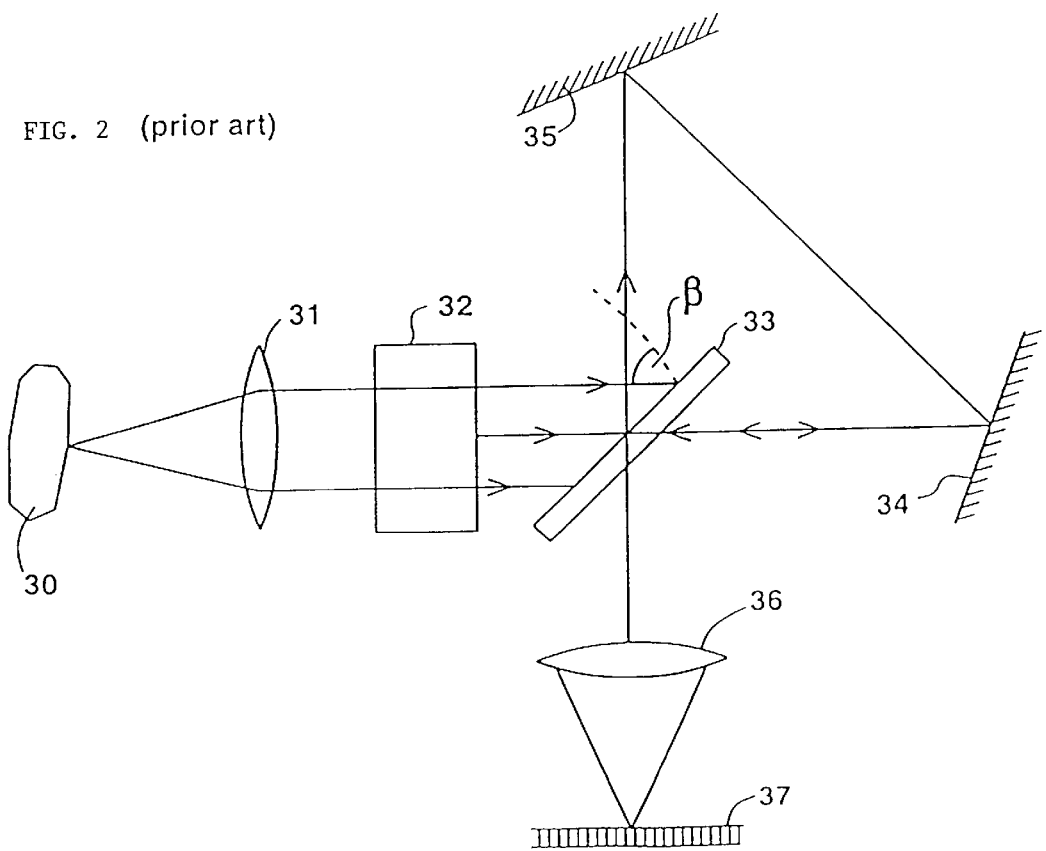
FIG. 2 illustrates a non-moving type interferometer, namely, a Sagnac interferometer, as used in an imaging spectrometer in accordance with U.S. patent application Ser. No. 08/392,019 (prior art).

FIG. 2 illustrates an imaging spectrometer constructed in accordance with U.S. Pat. No. 5,539,517, utilizing an interferometer in which the OPD varies with the angle of incidence of the incoming radiation. A beam entering the interferometer at a small angle to the optical axis undergoes an OPD which varies substantially linearly with this angle.

In the interferometer of FIG. 2, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle ($\sigma$) to the optical axis undergoes an OPD which is a function of the thickness of the beamsplitter 33, its index of refraction, and the angle $\sigma$. The OPD is proportional to $\sigma$ for small angles. By applying the appropriate inversion, and by careful bookkeeping, the spectrum of every pixel is calculated.

In the configuration of FIG. 2 the ray which is incident on the beamsplitter at an angle $\beta$ ($\beta=45°$ in FIG. 2) goes through the interferometer with an OPD=0, whereas a ray which is incident at a general angle $\beta-\sigma$ undergoes an OPD given by Equation 2:

$$OPD(\beta,\sigma,t,n)=t[(n^2-\sin^2(\beta+\sigma))^{0.5}-(n^2-\sin^2(\beta-\sigma))^{0.5}+2\sin\beta\sin\sigma] \quad (1)$$

where $\sigma$ is the angular distance of a ray from the optical axis or interferometer rotation angle with respect to the central position; t is the thickness of the beamsplitter; and n is the index of refraction of the beamsplitter.

It follows from Equation 2 that by scanning both positive and negative angles with respect to the central position, one gets a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

As mentioned above, an imaging spectrometer in accordance with the invention disclosed in U.S. Pat. No. 5,539,517 was developed by Applied Spectral Imaging Ltd., Industrial Park, Migdal Haemek, Israel and is referred herein as SPECTRACUBE™.

The SPECTRACUBE™ system has the following or better characteristics, listed hereinbelow in Table 3:

TABLE 3

| Parameter | Performance |
| --- | --- |
| Spatial resolution: | 30/M $\mu$m (M = effective microscope or fore optics magnification) |
| Field of View: | 15/M millimeters |
| Sensitivity: | 20 milliLux(for 100 msec integration time, increases for longer integration times linearly with $\sqrt{T}$ ) |
| Spectral range: | 400–1000 nm |
| Spectral resolution: | 4 nm at 400 nm (16 nm at 800 nm) |
| Acquistion time: | 5–50 sec, typical 25 sec |
| FFT processing time: | 20–180 sec, typical 60 sec |

The SPECTRACUBE™ system optically connected to a microscope is preferably used to analyze biological samples according to the method of the present invention. However, any spectral imager, i.e., an instrument that measures and stores in memory for later retrieval and analysis the spectrum of light emitted by every point of an object which is placed in its field of view, including filter (e.g., acousto-optic tunable filters (AOTF) or liquid-crystal tunable filter (LCTF)) and dispersive element (e.g., grating or prism) based spectral imagers, or other spectral data or multi-band light collection devices (e.g., a device in accordance with the disclosure in Speicher R. M., Ballard S. G. and Ward C. D. (1996) Karyotyping human chromosomes by combinatorial multi-flour FISH. Nature Genetics, 12:368–375) can be used to acquire the required spectral data. Also a device including a plurality of wide-band of (fixed or tunable), as described in U.S. patent application Ser. No. 08/917,213, filed Aug. 25, 1997, and is incorporated by reference as if fully set forth herein, can be used as the spectral data collection device according to the present invention. Therefore, it is intended not to limit the scope of the present invention for use of any specific type of spectral data collection devices, nor any specific type of spectral imager.

The power of the SPECTRACUBE™ system to resolve and differentiate between very similar spectra is demonstrated in FIGS. 3–5.

Figures 3A, 3B:
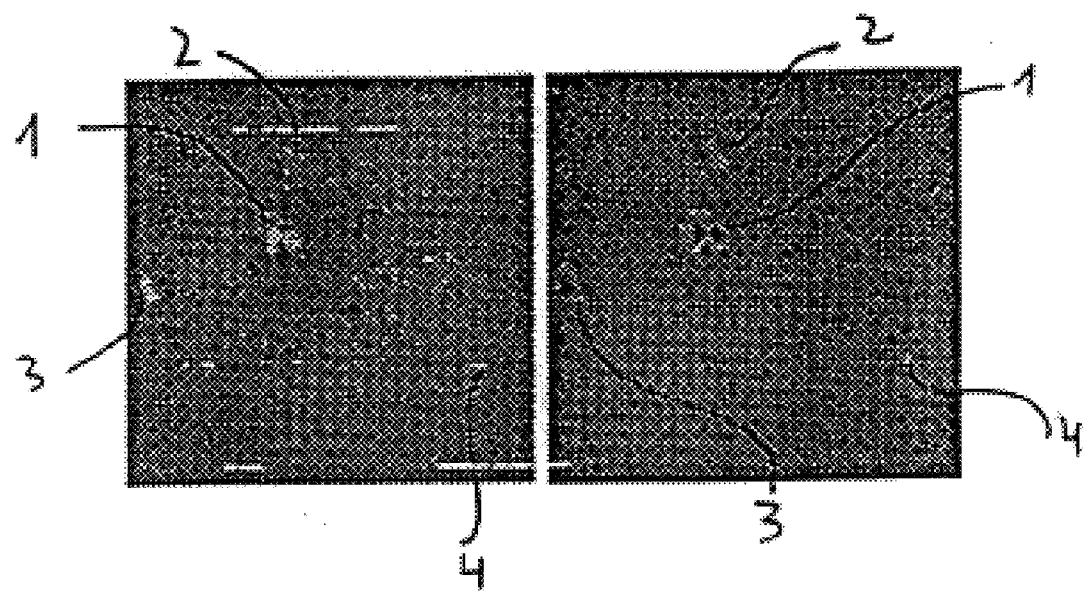
FIGS. 3a–c show interphase FISH performed with two different probes attached to Texas-Red and Rhodamine wherein (a) is an original image, the way it looks thorough a microscope; (b) is the same sample, after being measured and processed by the SPECTRACUBE™ system; and (c) are the fluorescence spectra of the Texas-Red and Rhodamine fluorophores.
Figure 3C:
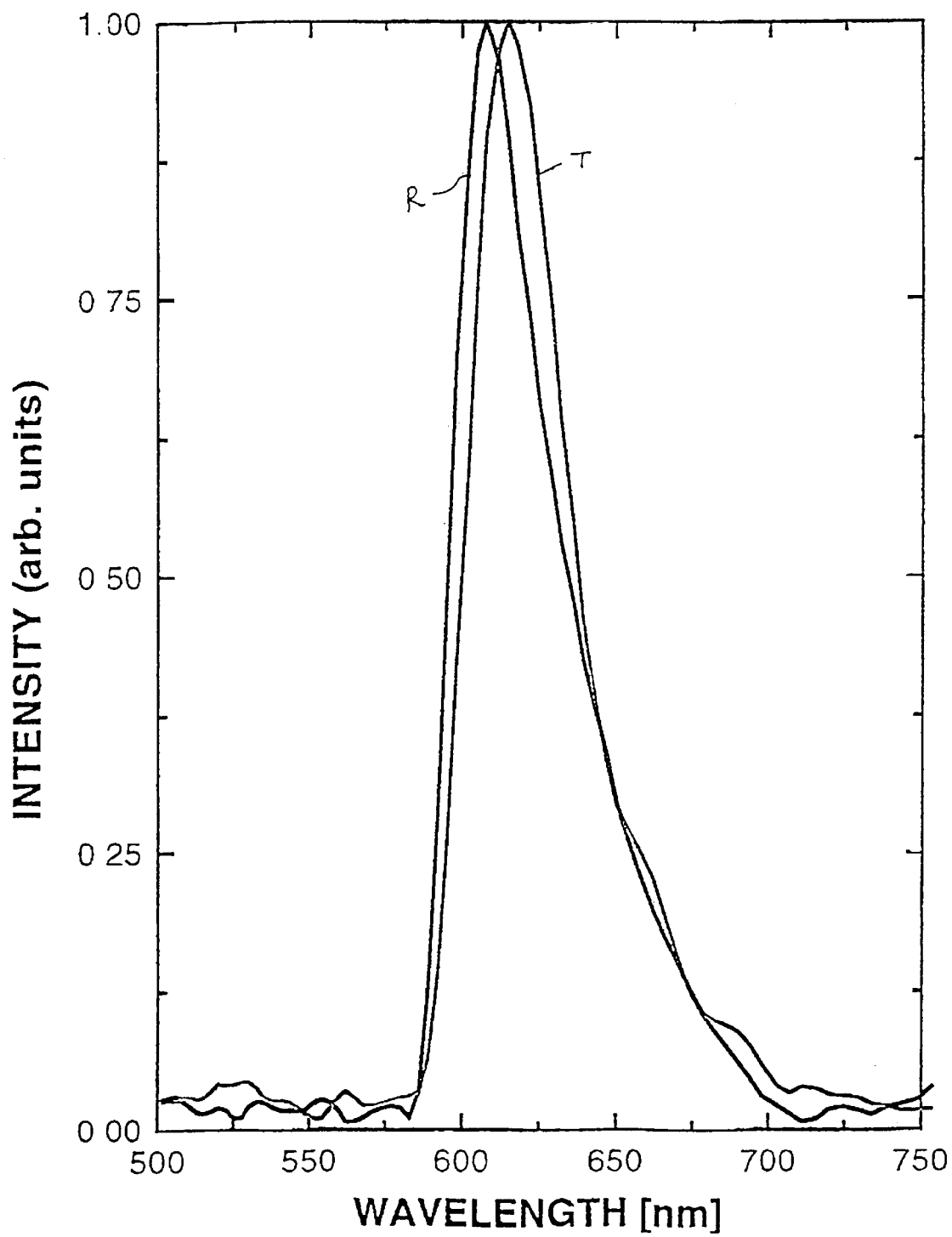

To illustrate this capability, the reader is first referred to FIGS. 3a–c, which include an example of an interphase FISH measurement performed with chromosome 1 and chromosome 17 specific DNA probes tagged with the fluorophores Texas-Red and Rhodamine, respectively, whose fluorescence spectra are very similar. The chromosome 1 probe was a midsatellite probe for the subtelomeric region of the chromosome and was tagged with Texas-Red linked to the DNA probe via biotin post hybridization. The chromosome 17 probe was an α satellite probe for the centromeric region of the chromosome and was tagged with Rhodamine, linked to the second DNA probe via digoxigenin post hybridization. FIG. 3a shows the original image, the way it looks to the eye through the microscope. FIG. 3b shows the same sample, after being measured and processed by the SPECTRACUBE™ system. Whereas FIG. 3c shows the fluorescence spectra of the Texas-Red (marked as T) and Rhodamine (marked as R) fluorophores.

As seen in FIG. 3c, the spectral peaks of Texas-Red and Rhodamine differ merely by 15 nm, and therefore it would be very difficult to distinguish between them using a filter-based system.

Looking at a color FISH image through a microscope as shown in FIG. 3a, the confidence level of recognizing the correct number of dots (marked 1–4) and of probe types appearing in the image is not particularly high. As shown in FIG. 3b, the SPECTRACUBE™ system, on the other hand, taking advantage of the spectrum measured for each pixel, is able both to verify the existence of the dots, to count them exactly, and to discriminate between the different pairs with a high level of confidence, due to the small spectral difference between them. By artificial coloring of Texas-Red and Rhodamine fluorescence, as shown in FIG. 3c the location of probe specific fluorescence could be determined with high accuracy wherein dots 1 and 2 are of Texas-Red and dots 3 and 4 are of Rhodamine.

Figure 4A:
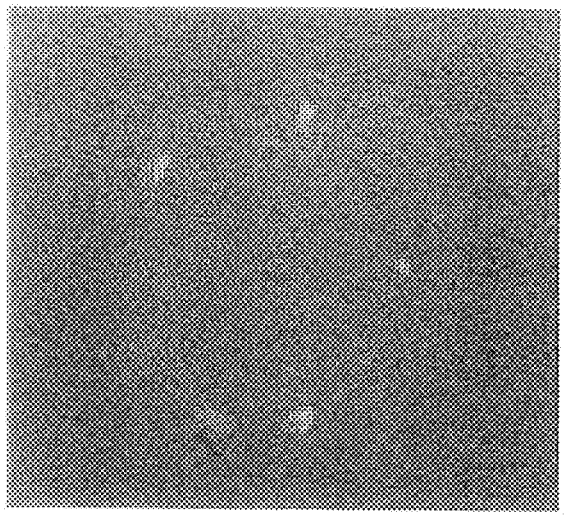
FIGS. 4a–c show interphase FISH performed using the SPECTRACUBE™ system with six different probes each labeled with a different fluorophore wherein (a) is an original image, the way it looks thorough a microscope, cells were counter stained with DAPI; (b) is the same sample, after being measured and processed by the SPECTRACUBE ™ system; and (c) are the fluorescence spectra of the six fluorophores which were employed for classification.
Figure 4B:
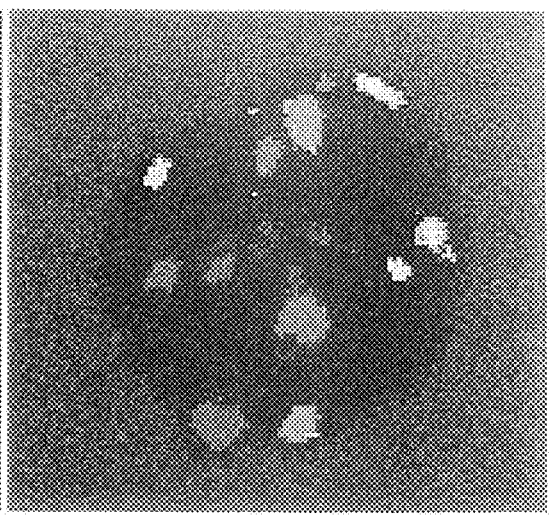
Figure 4C:
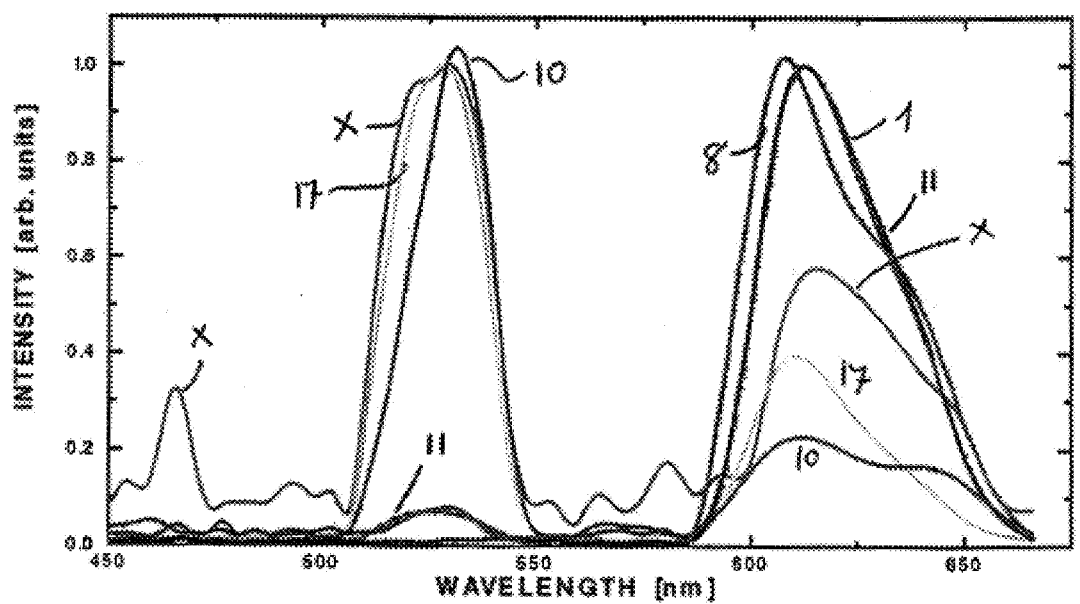

FIGS. 4a–b provide an example of FISH measurement after hybridization of nuclear interphase DNA with six different probes. FIG. 4a shows the original image as perceived through a microscope. FIG. 4b shows the same image following a SPECTRACUBE™ system measurement, spectral processing and artificial color display of all the detected pairs. FIG. 4c shows the spectra of the six fluorophores after hybridization (marked according to the chromosomes each of which labels: 1, 8, 10, 11, 17 and X), as detected through a triple dichroic filter using the SPECTRACUBE™ system. For details regarding fluorophores, probes and chromosomes the reader is referred to the following description, Table 3 below and to Chroma Corp. Cat. No. 61502).

It is apparent from FIG. 4a, showing the original RGB image of the interphasic cell nucleus, that it is difficult to distinguish the colors from one another by eye or even by using a simple RGB color measurement.

An experienced observer may, in the best case, detect three different colors of the six. FIG. 4b, however, shows the same sample shown in FIG. 4a, after processing the spectral data with a classification algorithms, and the resulting dots have been highlighted with artificial colors: orange, cyan, blue, yellow, green, and red, while the background was given a black, artificial color. As observed, it is possible to see all the six pairs of fluorophores and to easily differentiate among the pairs.

It should be further noted that one pair, the one highlighted in blue, can hardly be noticed by eye, or by using a color camera, however, it is detected after applying a background subtraction algorithm on the spectral cube (compare FIGS. 4a and 4b).

The probes used were five a satellite probes for the centromeric regions of chromosomes 8, 10, 11, 17 and X, and a midsatellite probe for the subtelomeric region of chromosome 1. The fluorophores used to label each of the above chromosomes and the DAPI counter stain (background), their emission peak and artificial displayed color classification are summarized in Table 4, below.

From the normalized spectral signatures of each of the six fluorophores shown in FIG. 4c, it is clear that a system based on filters measuring at a few relatively wide spectral ranges, is not able to differentiate reliably between the different probe species, because of the large overlap between their spectra. Such a system is more dependent on the absolute measurement of the intensity of each probe, and therefore it is more affected by background signals and noise. It should be further noted that spectral overlapping sometimes occurs also with auto-fluorescence originating from the cell itself. In this case too, the availability of spectral information for each pixel enables the elimination of the auto-fluorescence contribution, and yields more accurate results.

TABLE 4

| Chromosome | Fluorophore | Emission peak | Displayed color |
|---|---|---|---|
| 8 | SpectrumOrange ™ [1] | 588 nm | Brown |
| 10 | SpectrumGreen ™ [1] | 538 nm | Cyan |
| x | Aqua[1] | 480 nm | Blue |
| 1 | Texas-Red[2] | 615 nm | Yellow |
| 17 | FITC[3] | 525 nm | Green |
| 11 | Texas-Red[2] + FITC[3] | 615, 525 nm | Red |
| backg. | DAPI[4] | | Black |

[1]obtained as labeled deoxynucleotides from Vysis, Downers Grove, IL, U.S.;
[2]conjugated via anti-digoxigenin antibody to pre hybridized digoxigenin containing probes;
[3]fluorescein-5-iso-thiocyanate, conjugated via anti-biotin antibody to pre hybridized biotin containing probes;
[4]4',6-diamidino-2-phenylindole used for counter staining.

Figure 5A:
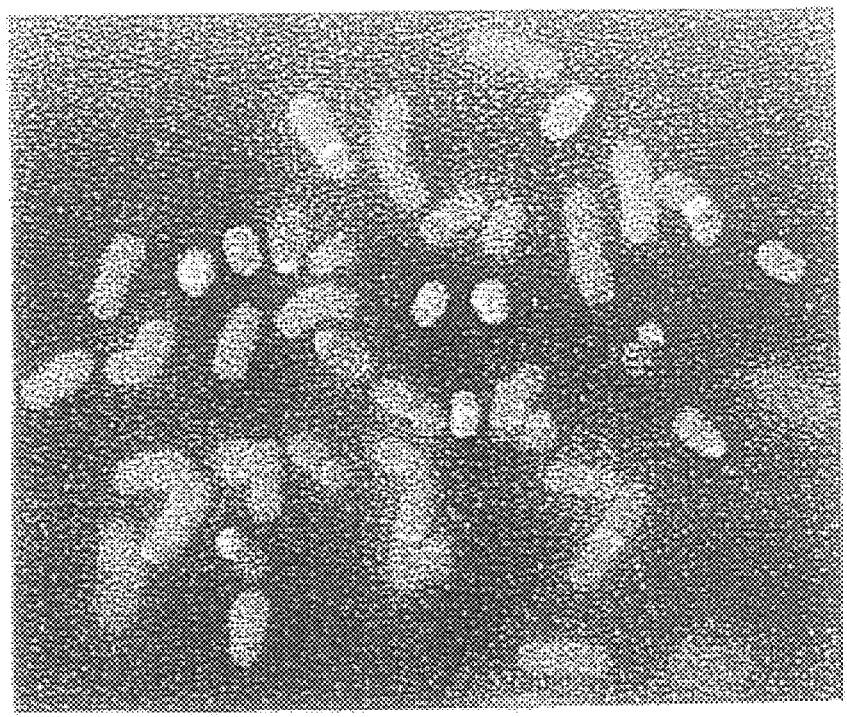
Figure 5B:
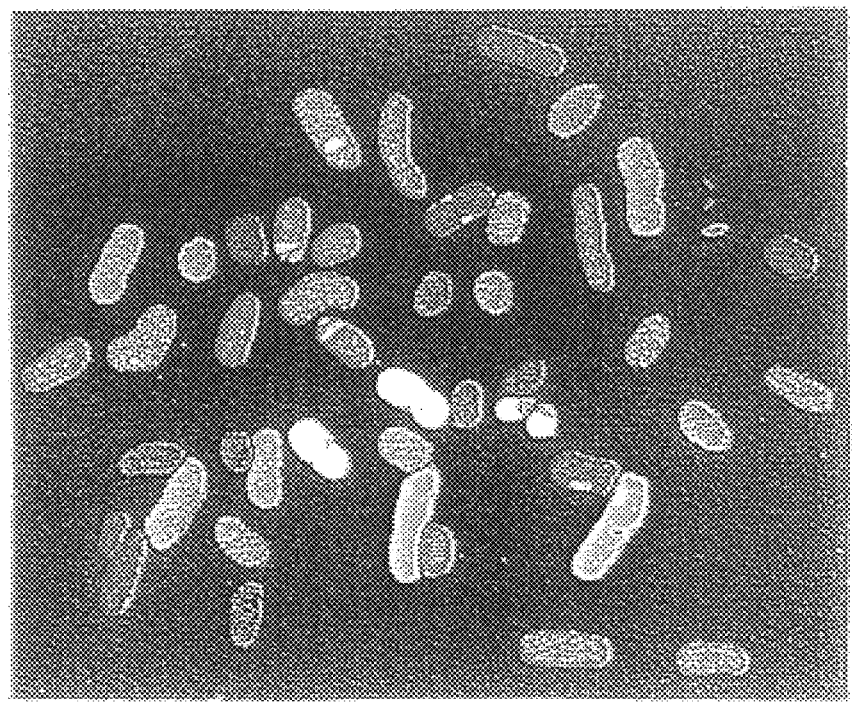
Figure 5C:
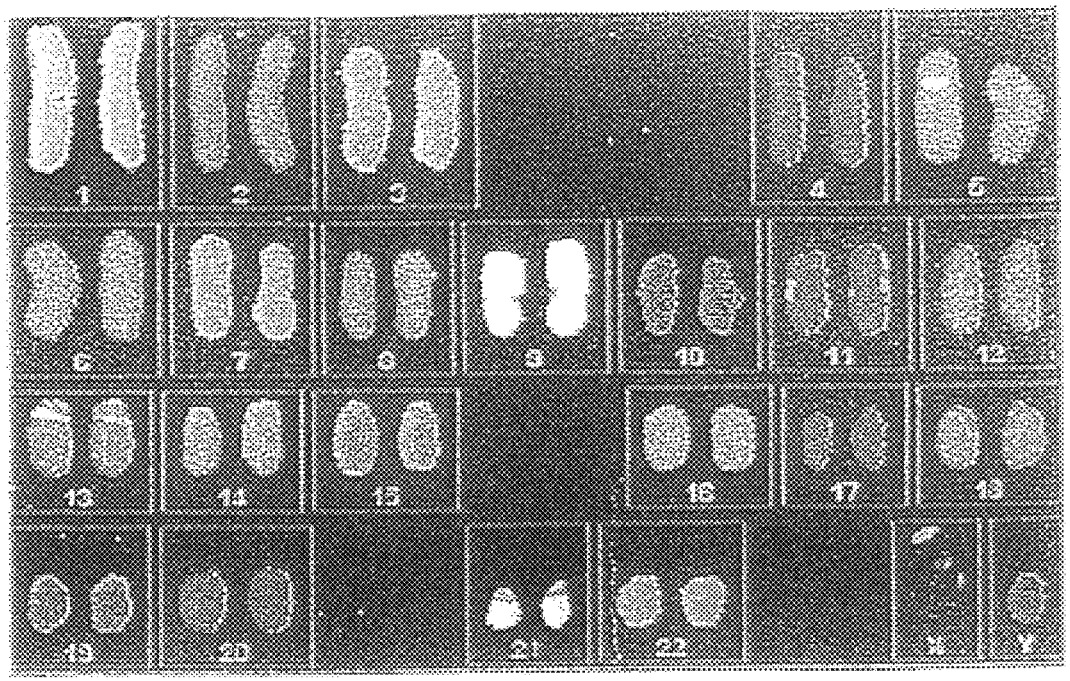

FIGS. 5a–c present hybridization results of normal male chromosomes using a combinatorial hybridization approach in accordance with the scheme disclosed in U.S. patent application Ser. No. 09/025,131, filed Feb. 17, 1998, which is incorporated by reference as if fully set forth herein.

FIG. 5a is an RGB image of the chromosome spread obtained using an RGB algorithm. The RGB algorithm integrates the optical signal over the spectral range (e.g., 400 nm to 760 nm) of the CCD array to provide an RGB image of the chromosomes, in which each pixel is attributed a combination of red, green and blue intensities according to three weighting functions, $\{w_r(\lambda), w_g(\lambda), w_b(\lambda)\}$, which correspond to the tristimulus response functions for red (R), green (G) and blue (B).

In FIG. 5q, the weighting functions $w_r, w_g, w_b$, employed were simple square weighting functions, wherein for $w_r$ (red) $\lambda_1=640$ nm and $\lambda_2=750$ nm; for $w_g$ (green) $\lambda_1=555$ nm and $\lambda_2=640$ nm; and for $w_b$ (blue) $\lambda_1=450$ nm and $\lambda_2=555$ nm. The simple weighting functions $w_r, w_g, w_b$ are integrated to generate an RGB image of the chromosomes.

FIGS. 5b is a classification image of the chromosome spread of FIG. 5a. FIG. 5c is the karyotype derived from the chromosome spread of FIG. 5b. The classification image is calculated by a classification algorithm wherein each pixel is classified according its spectrum. One of the most important analysis algorithms is the spectral-based classification algorithm that enables multiple different spectra in the image to be identified and highlighted in classification-colors. This allows assignment of a specific classification-color to all human chromosomes based on their spectra. This algorithm assumes that a reference spectrum of each chromosome has been measured and stored in a reference library in the computer. A distinguishing classification-color is assigned to each pixel in the image according to the classification-color assigned to the reference spectrum that is most similar to the spectrum at that given pixel, as defined, for example, by a minimal square error algorithm.

Example 2

Analyzing and Displaying the Results

General: A spectral image is a three dimensional array of data, $I(x,y, \lambda)$, that combines spectral information with spatial organization of the image. As such, a spectral image is a set of data called a spectral cube, due to its dimensionality, which enables the extraction of features and the evaluation of quantities that are difficult, and in some cases even impossible, to obtain otherwise. Since both spectroscopy and digital image analysis are well known fields that are covered by an enormous amount of literature [see, for example, Jain (1989) Fundamentals of Digital Image Processing, Prentice-Hall International], the following discussion will focus primarily on the benefit of combining spectroscopic and imaging information in a single data set i.e., a spectral cube.

One possible type of analysis of a spectral cube is to use spectral and spatial data separately, i.e., to apply spectral algorithms to the spectral data and two-dimensional image processing algorithms to the spatial data.

As an example of a spectral algorithm, consider an algorithm computing the similarity between a reference spectrum and the spectra of all pixels (i.e., similarity mapping) resulting in a gray (or other color) scale image (i.e., a similarity map) in which the intensity at each pixel is proportional to the degree of 'similarity'. This gray scale image can then be further analyzed using image processing and computer vision techniques (e.g., image enhancement, pattern recognition, etc.) to extract the desired features and parameters. In other words, similarity mapping involves computing the integral of the absolute value of the difference between the spectrum of each pixel of the spectral image with respect to a reference spectrum (either previously memorized in a library, or belonging to a pixel of the same or other spectral image), and displaying a gray level or pseudocolor (black and white or color) image, in which the bright pixels correspond to a small spectral difference, and dark pixels correspond to a large spectral difference, or vice versa.

Similarly, classification mapping perform the same calculation as described for similarity mapping, yet takes several spectra as reference spectra, and paints each pixel of the displayed image with a different predetermined pseudocolor, according to its classification as being most similar to one of the several reference spectra.

It is also possible to apply spectral image algorithms based on non-separable operations; i.e., algorithms that include both local spectral information and spatial correlation between adjacent pixels (one of these algorithms is, as will be seen below, a principal component analysis).

One of the basic needs that arise naturally when dealing with any three-dimensional (3D) data structure such as a spectral cube (i.e., $I(x,y,\lambda)$), is visualizing that data structure in a meaningful way. Unlike other types of 3D data such as topographic data, $D(x,y,z)$, obtained for example by a confocal microscope, where each point represents, in general, the intensity at a different location $(x,y,z)$ in a tree-dimensional space, a spectral image is a sequence of images representing the intensity of the same two-dimensional plane (i.e., the sample) at different wavelengths. For this reason, the two most intuitive ways to view a spectral cube of data is to either view the image plane (spatial data) or the intensity of one pixel or a set of pixels as function of wavelength in a three-dimensional mountain-valley display. In general, the image plane can be used for displaying either the intensity measured at any single wavelength or the gray scale image that results after applying a spectral analysis algorithm, over a desired spectral region, at every image pixel. The spectral axis can, in general, be used to present the resultant spectrum of some spatial operation performed in the vicinity of any desired pixel (e.g., averaging the spectrum).

It is possible, for example, to display the spectral image as a gray scale image, similar to the image that might be obtained from a simple monochrome camera, or as a multicolor image utilizing one or several artificial colors to highlight and map important features. Since such a camera simply integrates the optical signal over the spectral range (e.g., 400 nm to 760 nm) of the CCD array, the 'equivalent' monochrome CCD camera image can be computed from the 3D spectral image data base by integrating along the spectral axis, as follows:

$$\text{gray\_scale}(x, y) = \int_{\lambda 1}^{\lambda 2} w(\lambda) \cdot I(x, y, \lambda) d\lambda \qquad (2)$$

Figure 6:
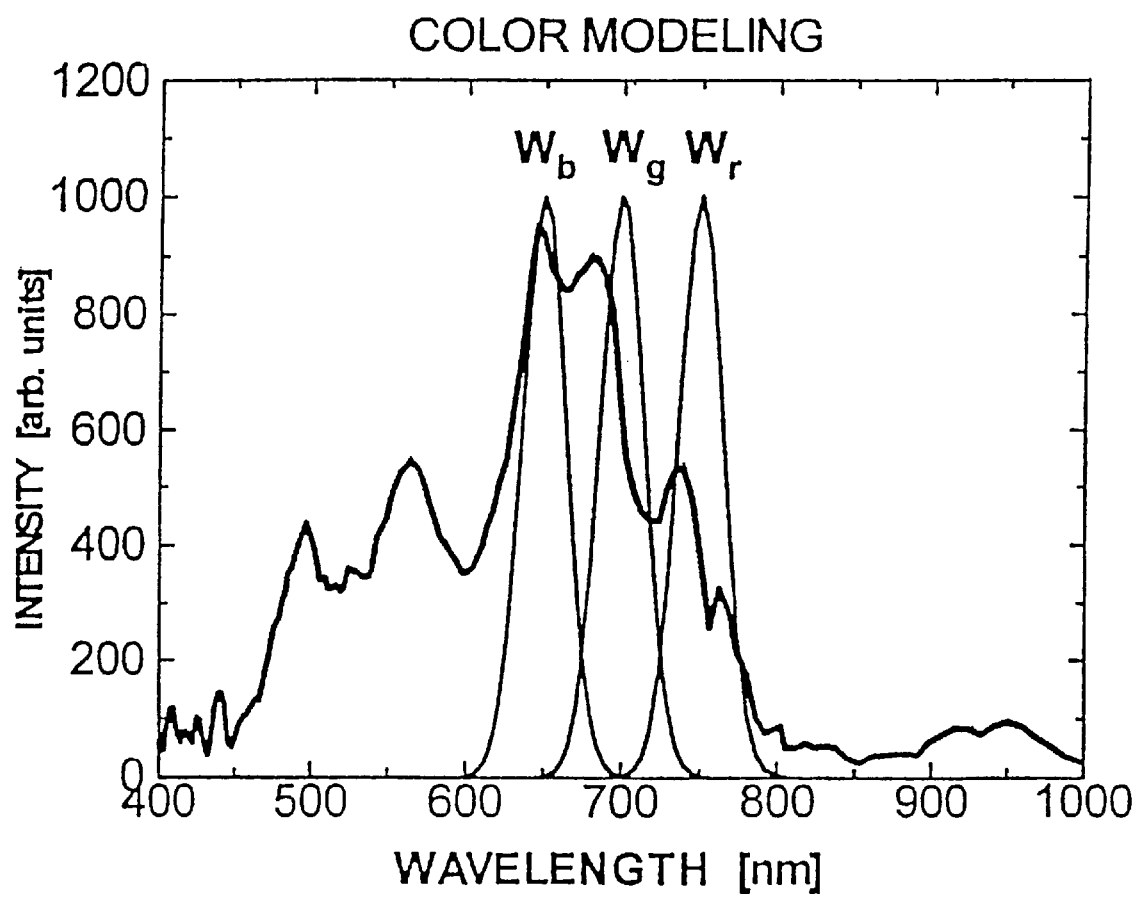
FIG. 6 shows a definition of pseudo-RGB (Red, Green and Blue) colors for emphasizing chosen spectral ranges. The intensity for each pseudo-color is calculated by integrating the area under the curve, after multiplying it by one of the curves.

In equation 2, $w(\lambda)$ is a general weighting response function that provides maximum flexibility in computing a variety of gray scale images, all based on the integration of an appropriately weighted spectral image over some spectral range. For example, by evaluating equation 2 with three different weighting functions, $\{w_r(\lambda), w_g(\lambda), w_b(\lambda)\}$, corresponding to the tristimulus response functions for red (R), green (G) and blue (B), respectively, it is possible to display a conventional RGB color image. It is also possible to display meaningful non-conventional (pseudo) color images. FIG. 6 presents an example of the power of this simple algorithm. Consider choosing $\{w_r, w_g, w_b\}$ to be Gaussian functions distributed "inside" a spectrum of interest, the resulting pseudo-color image that is displayed in this case emphasizes only data in the spectral regions corresponding to the weighting functions, enabling spectral differences in these three regions to be detected more clearly.

Point operations: Point operations are defined as those that are performed on single pixels, (i.e., do not involve more than one pixel at a time). For example, in a gray scale image, a point operation can be one that maps the intensity of each pixel (intensity function) into another intensity according to a predetermined transformation function. A particular case of this type of transformation is the multiplication of the intensity of each pixel by a constant. Additional examples include similarity and classification mapping as described hereinabove.

The concept of point operations can also be extended to spectral images: here each pixel has its own intensity function (spectrum), i.e., an n-dimensional vector $V_1(\lambda)$; $\lambda \epsilon [\lambda_1, \lambda_n]$. A point operation applied to a spectral image can be defined as one that maps the spectrum of each pixel into a scalar (i.e., an intensity value) according to a transformation function:

$$v_2 = g(V_1(\lambda)); \lambda \epsilon [\lambda_1, \lambda_n] \qquad (3)$$

Building a gray scale image according to Equation 3 is an example of this type of point operation. In the more general case, a point operation maps the spectrum (vector) of each pixel into another vector according to a transformation function:

$$V_2(l) = g(V_1(\lambda)); \; l \in [1, N], \; \lambda \in [\lambda_1, \lambda_n] \qquad (4),$$

where $N \leq n$.

In this case a spectral image is transformed into another spectral image.

One can now extend the definition of point operations to include operations between corresponding pixels of different spectral images. An important example of this type of algorithm is optical density analysis. Optical density is employed to highlight and graphically represent regions of an object being studied spectroscopically with higher dynamic range than the transmission spectrum. The optical density is related to transmission by a logarithmic operation and is therefore always a positive function. The relation between the optical density and the measured spectra is given by Lambert Beer law:

$$OD(\lambda) = -\log_{10} \frac{I(\lambda)}{I_0(\lambda)} = -\log_{10} \tau(\lambda) \qquad (5)$$

where $OD(\lambda)$ is the optical density as a function of wavelength, $I(\lambda)$ is the measured spectrum, $I_O(\lambda)$ is a measured reference spectrum, and $\tau(\lambda)$ is the spectral transmittance of the sample. Equation 5 is calculated for every pixel for every wavelength where $I_O(\lambda)$ is selected from (1) a pixel in the same spectral cube for which OD is calculated; (2) a corresponding pixel in a second cube; and (3) a spectrum from a library.

Note that the optical density does not depend on either the spectral response of the measuring system or the non-uniformity of the CCD detector. This algorithm is useful to map the relative concentration, and in some cases the absolute concentration of absorbers in a sample, when their absorption coefficients and the sample thickness are known.

Additional examples include various linear combination analyses, such as, but not limited to, (i) applying a given spectrum to the spectrum of each of the pixels in a spectral image by an arithmetical function such as addition, subtraction, multiplication division and combinations thereof to yield a new spectral cube, in which the resulting spectrum of each pixel is the sum, difference, product ratio or combination between each spectrum of the first cube and the selected spectrum; and (ii) applying a given scalar to the spectra of each of the pixels of the spectral image by an arithmetical function as described above.

Such linear combinations may be used, for example, for background subtraction in which a spectrum of a pixel located in the background region is subtracted from the spectrum of each of the pixels; and for a calibration procedure in which a spectrum measured prior to sample analysis is used to divide the spectrum of each of the pixels in the spectral image.

Another example includes a ratio image computation and display as a gray level image. This algorithm computes the ratio between the intensities at two different wavelengths for every pixel of the spectral image and paints each of the pixels in a lighter or darker artificial color accordingly. For example, it paints the pixel bright for high ratio, and dark for low ratio (or the opposite), to display distributions of spectrally sensitive materials.

Spatial-spectral combined operations: In all of the spectral image analysis methods mentioned above, algorithms are applied to the spectral data. The importance of displaying the spectrally processed data as an image is mostly qualitative, providing the user with a useful image. It is also possible, however, depending on the application, to use the available imaging data in even more meaningful ways by applying algorithms that utilize the spatial-spectral correlation that is inherent in a spectral image. Spatial-spectral operations represent the most powerful types of spectral image analysis algorithms. As an example, consider the following situation:

A sample contains k cell types stained with k different stains (the term 'cell' here is used both for a biological cell, and also as 'a region in the field of view of the instrument'). Each stain has a distinct spectrum and binds to only one of the k cell types. It is important to find the average intensity per cell for each one of the k cell types. To achieve this task the following procedure can be used: (i) classify each pixel in the image as belonging to one of k+1 classes (k cell types plus a background) according to its spectrum; (2) segment the image into the various cell types and count the number of cells from each type; and (3) sum the spectral energy contributed by each class, and divide it by the total number of cells from the corresponding class.

This procedure makes use of both spectral and spatial data. The relevant spectral data takes the form of characteristic cell spectra (i.e., spectral "signatures"), while the spatial data consists of data about various types of cells (i.e., cell blobs) many of which appear similar to the eye. In the above situation, cells can be differentiated by their characteristic spectral signature. Hence, a suitable point operation will be performed to generate a synthetic image in which each pixel is assigned one of k+1 values. Assuming that the spectra of the different cell types are known to be $s_i(\lambda)$; i=1, 2, . . . , k, $\lambda \in [\lambda_1, \lambda_n]$, and the measured spectrum at each pixel (x,y) is $s_{x,y}(\lambda)$, $\lambda \in [\lambda_1, \lambda_n]$, then the following algorithm is a possible method of classification (step 1 above):

Let $e^2_i$ be the deviation of the measured spectrum from the known spectrum of the stain attached to cell type i. Then, adopting a least-squares "distance" definition, one can write:

$$e_i^2 = \sum_{\lambda \in R_\lambda} (s(\lambda) - s_i(\lambda))^2 \qquad (6)$$

where $R_\lambda$ is the spectral region of interest. Each point [pixel (x, y)] in the image can then be classified into one of the k+1 classes using the following criterion:

$$\text{point}(x,y) \in \text{class } k+1 \text{ if } e^2_i > \text{threshold for all } i \in [1,k], \qquad (7)$$

whereas point(x,y) $\in$ class $\rho$ if $e^2_i$<threshold, and $\rho$ is such that $\min[e^2_i] = e^2_\rho$ Steps 2 and 3 above (image segmentation and calculation of average intensity) are now straight-forward using standard computer vision operations on the synthetic image created in accordance with the algorithm described in equations 6 and 7.

Another approach is to express the measured spectrum $s_{x,y}(\lambda)$ at each pixel as a linear combination of the k known fluorescence spectra $s_i(\lambda)$; i=1, 2, . . . , k. In this case one would find the coefficient vector $C=[c_1, c_2, \ldots, c_k]$ that solves:

$$F = \min \sum_{\lambda \in R_\lambda} (s(\lambda) - \hat{s}(\lambda))^2 \qquad (8)$$

where $$\hat{s}(\lambda) = \sum_{i=1}^{k} c_i \cdot s_i(\lambda),$$

Solving for $$\frac{dF}{dc_i} = 0;$$

for i=1,2, . . . , k(i.e., find values of $c_i$ which minimize F) yields the matrix equation C=A$^{-1}$B (9), where A is a square matrix of dimension k with elements $$a_{m,n} = \left[ \sum_{\lambda \in R_\lambda} s_m(\lambda) \cdot s_n(\lambda) \right], \qquad (10)$$

and B is a vector defined as $$b_m = \left[ \sum_{\lambda \in R_\lambda} s_m(\lambda) \cdot s(\lambda) \right], \qquad (11)$$

$$m, n = 1, 2, \ldots, k.$$

Arithmetic operations may similarly be applied to two or more spectral cubes and/or spectra of given pixels or from a library. For example consider applying an arithmetic operations between corresponding wavelengths of corresponding pairs of pixels belonging to a first spectral cube of data and a second spectral cube of data to obtain a resulting third spectral cube of data for the purpose of, for example, averaging two spectral cubes of data, time changes follow-up, spectral normalization, etc.

In many cases objects (e.g., cells) present in a spectral image differ from one another in chemical constituents and/or structure to some degree, especially when stained. Using a decorrelation analysis, such as a principal component analysis, by producing covariance or a correlation matrix, enhances these differences. Decorrelation statistical analysis is directed at extracting decorrelated data out of a greater amount of data, and average over the correlated portions thereof. There are a number of related statistical decorrelation methods. Examples include but not limited to principal component analysis (PCA), canonical variable analysis and singular value decomposition, etc., of these methods PCA is perhaps the more common one, and is used according to the present invention for decorrelation of spectral data, as this term is defined above. However, considering the fact that all decorrelation statistical methods including those listed above are related to one another, there is no intention to limit the scope of the invention to use of any specific decorrelation method. Specifically, there is no intention to limit the scope of the present invention to use of principal component analysis, as any other decorrelation statistical method may be alternatively employed. Information concerning the use and operation of the above listed decorrelation statistical methods is found in R. A. Johnson and D. W. Wichen, "Applied Multivariance Statistical Analysis", third edition, Prentice Hall (1992) and T. W. Anderson, An Introduction to Multivariance Statistical Analysis, second edition, Wiley and Sons (1984), both are incorporated by reference as if fully set forth herein.

Furthermore, as will become apparent from the descriptions to follow, the implementation of a decorrelation statistical method may be done using various modifications. As the concept of the present invention is not dependent upon any specific modification, it is the intention that the scope of the present invention will not be limited to any specific modification as described below.

A brief description of the principal component analysis using a covariance matrix is given below. For further details regarding the principal component analysis, the reader is referred to Martens and Naes (1989) Multivariate Calibration, John Wiley & Sons, Great Britain; and to Esbensen et al., Eds. (1994) Multi variance analysis—in practice. Computer-aided modeling as CAMO, and the Unscrambler's User's guide, Trondheim, Norway.

Thus, the intensities of the pixels of the image at wavelength $\lambda_i$(i=1, . . . N) are now considered a vector whose length is equal to the number of pixels q. Since there are N of these vectors, one for every wavelength of the measurement, these vectors can be arranged in a matrix B' with q rows, and N columns:

$$B' = \begin{matrix} & \text{No. of wavelengths} & (12) \\ \text{No. of pixels} & \begin{bmatrix} B'_{11} & \cdots & B'_{1N} \\ \vdots & & \vdots \\ B'_{q1} & \cdots & B'_{qN} \end{bmatrix} \end{matrix}$$

For each of the columns of matrix B' defined is an average:

$$M_i = \frac{1}{q} \sum_{i=1}^{q} B'_{ji}; \; i = 1 \ldots N \qquad (13)$$

and a second normalized matrix B defined as:

$$B = \begin{matrix} & \text{No. of wavelengths} & (14) \\ \text{No. of pixels} & \begin{bmatrix} B'_{11}/M_1 & \cdots & B'_{1N}/M_N \\ \vdots & & \vdots \\ B'_{q1}/M_1 & \cdots & B'_{qN}/M_N \end{bmatrix} \end{matrix}$$

A covariance matrix C is defined for the matrix B: C=B$^T$.B of dimensions N×N. C is diagonalized, and eigenvectors and eigenvalues related by: C.$V_i=\mu_i V_i$ where Vi are N orthogonal unit vectors and $\mu_i$ are the eigenvalues representing the variance in the direction of the i-th unit vector $V_i$. In general, the lowest components represent the highest variability as a function of pixels.

The products BV$_i$(i=1, . . . N) are the projections of the spectral image onto the elements of the orthogonal basis, They are vectors with q elements (q=number of pixels), and can be displayed separately as black and white images. These images may reveal features not obvious from a regular black and white image filtered at a certain wavelength or wavelength range.

Example 3

Materials and Methods

Breast cancer:

Sample: All samples were obtained by from a 79 woman suffering from infiltrating ductal carcinoma, moderately differentiated. Samples were cross sectioned and prepared for staining following conventional protocols.

Staining protocols: Staining was performed following standard Vantana or DAKO automated immunostaining protocols.

Measurement: A microscope (Nikon Eclipse E-800) connected to a SPECTRACUBE™ system was adjusted for Koehler illumination with transmitted light lamp power to maximum voltage (12 V) for most stable illumination. Neutral density and color filters (FG3 and anti reflection filters) were introduced in the optical path to adjust intensity and spectral color balance. SPECTRACUBE acquisition parameters were 300 frames, 512 virtual frames, wavelength range 440 to 760 nm, 176 ms/frame.

First, "pure dye" i.e., hematoxylin, DAB, AEC and Fast Red (each stain alone) spectral cubes were acquired and representative spectra therefrom were used to form pure dyes spectral library.

Then spectral cubes of each of the samples were acquired. And the SPECTRACUBE™ algorithms SpyView, as described in the SPECTRACUBE™ manual were employed to obtain RGB images, gray-level images of each spectral component, threshold binarized images and composite classification images thereof.

Cervix cancer:

Sample: A pap smear of a middle aged woman was collected following conventional procedures.

Staining protocols: Staining was essentially as described in G. Papanicolaou (1942) A new procedure for staining vaginal smears. Science 95: 438–439, which is incorporated by reference as if fully set forth herein.

Measurement: A microscope (Nikon Eclipse E-800) connected to a SPECTRACUBE™ system was adjusted for Koehler illumination with transmitted light lamp power to maximum voltage (12 V) for most stable illumination. Neutral density and color filters (FG3 and anti reflection filters) were introduced in the optical path to adjust intensity and spectral color balance. SPECTRACUBE acquisition parameters were 300 frames, 512 virtual frames, wavelength range 440 to 760 nm, 176 ms/frame.

First, "pure dye" i.e., Harris hematoxylin, eosin, orange G, light green SF and Bismark brown Y (each stain alone) spectral cubes were acquired and representative spectra therefrom were used to form pure dyes spectral library.

Then spectral cubes of the cervix cancer sample were acquired. And the SPECTRACUBE™ algorithms SpyView, as described in the SPECTRACUBE™ manual were employed to obtain RGB images, gray-level images of each spectral component, threshold binarized images and composite classification images thereof.

Example 4

Experimental Results

Two well characterized experimental models served to demonstrate the feasibility and applicability of the methods according to the present invention: breast cancer and cervix cancer samples.

Figure 7:
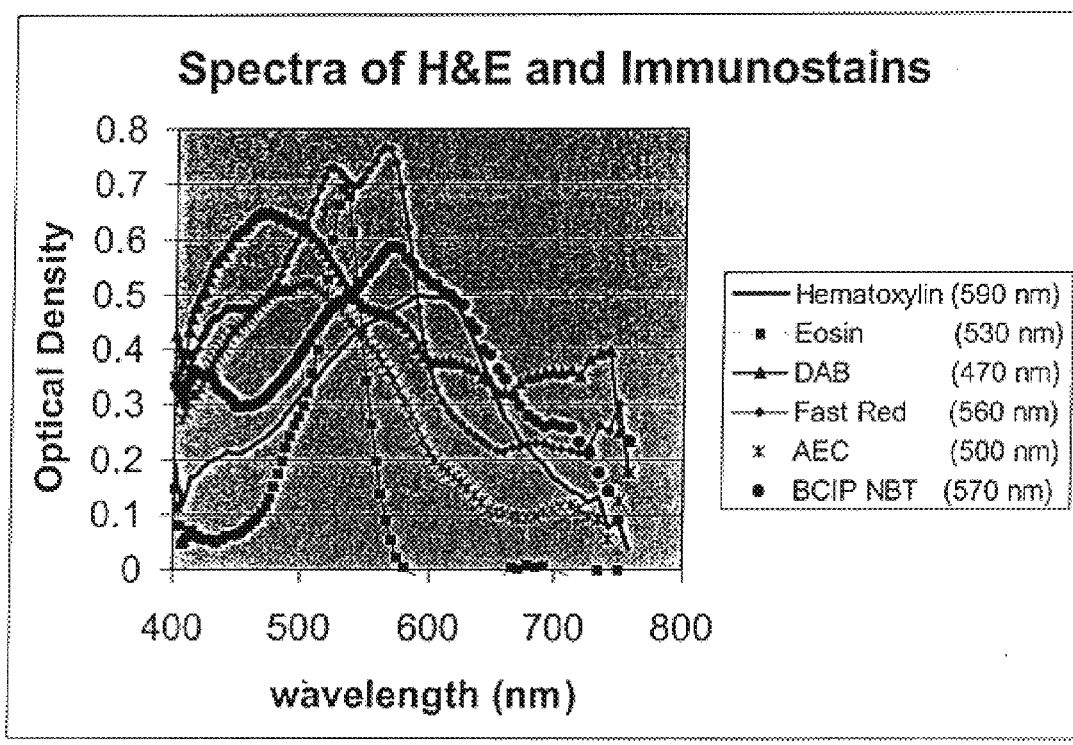
FIG. 7 presents non-normalized spectra of two histological stains (hematoxylin and eosin) and of four immunohistochemical stains (DAB, Fast Red, AEC and BCIP/NBT) measured using the SPECTRACUBE™ system from six single stain stained breast cancer samples. Peak wavelengths are indicated on the right.

FIG. 7 presents non-normalized spectra of two histological stains (hematoxylin and eosin) and of four immunohistochemical stains (DAB, Fast Red, AEC and BCIP/NBT) measured using the SPECTRACUBE™ system from six single stain stained breast cancer samples. Peak wavelengths are indicated on the right. Please note that each of the stains has a characterizing spectrum, which, as further exemplified hereinbelow, enables simultaneous co-detection of spectral components associated with each of which.

FIGS. 8–11 show such experiments. All images were measured using the SPECTRACUBE™ system and its various measurement and analysis algorithms, as described hereinabove.

Figure 8A:
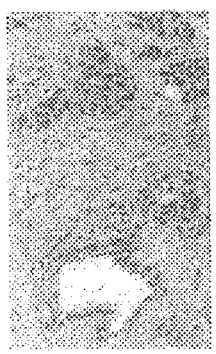
Figure 8B:
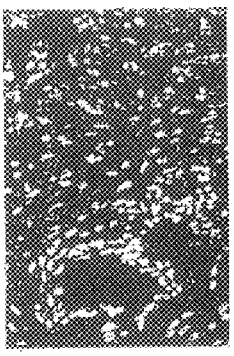
Figure 8C:
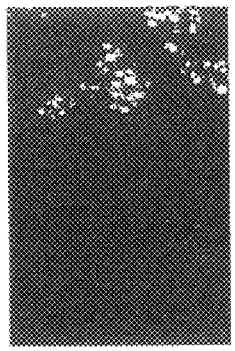
Figure 8D:
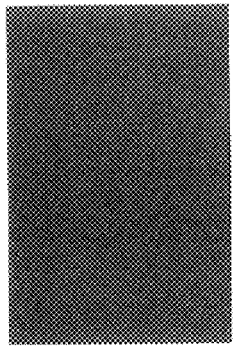
Figure 8E:
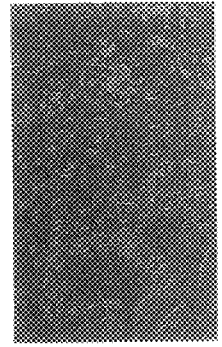

FIGS. 8a–e show images of a breast cancer sample which was previously and independently determined to be ER(+)/PR(+). The sample was co-stained with the histological stain hematoxylin and with the immunohistochemical stain anti-ER-DAB. FIG. 8a presents an RGB image of the sample, using the RGB algorithm described hereinabove with respect to FIG. 6. FIGS. 8b–d present binarized images of hematoxylin, DAB and AEC spectral components, respectively. These binarized images were obtained by thresholding gray-scale images showing the intensity of each component in each pixel. FIG. 8d serves as a simulation for a PR(−) tumor. FIG. 8e presents a classification overlay image, wherein the above spectral components are highlighted in red, green and blue, respectively. Please note that as expected no AEC spectral components are detectable, yet, spectral components of both hematoxylin and DAB are readily detectable. The classification image assists the pathologist in evaluating the presence/absence/aggression level/diagnosis and/or prognosis of cancer cells or tissue examined.

FIGS. 9a–e show images of a breast cancer sample which was previously and independently determined to be ER(+)/PR(+). This sample was also co-stained with the histological stain hematoxylin and with the immunohistochemical stain anti-PR-AEC. FIG. 9a presents an RGB image of the sample. FIGS. 9b–d present binarized images of hematoxylin, DAB and AEC spectral components, respectively, whereas FIG. 9e presents a classification overlay image, wherein the above spectral components are highlighted in red, green and blue, respectively.

Please note that as expected no DAB spectral components are detectable, yet, spectral components of both hematoxylin and AEC are readily detectable.

Figure 10A:
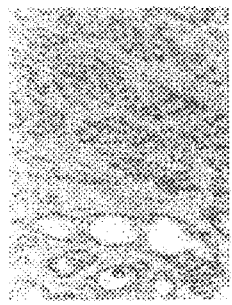
Figure 10B:
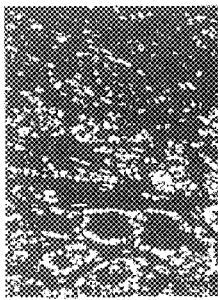
Figure 10C:
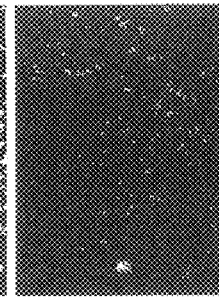
Figure 10D:
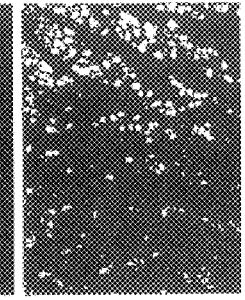
Figure 10E:
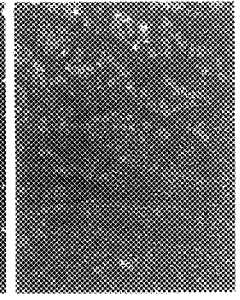

FIGS. 10a–e show images of a breast cancer sample which, like the former sample, was previously and independently determined to be ER(+)/PR(+). However, in this case the sample was co-stained with the histological stain hematoxylin and with the immunohistochemical stain anti-PR-Fast Red, which replaced the AEC previously used. FIG. 10a presents an RGB image of the sample. FIGS. 10b–d present binarized images of hematoxylin, DAB and Fast Red spectral components, respectively. FIG. 10e presents a classification overlay image, wherein the above spectral components are highlighted in red, green and blue, respectively. Please note that as expected no DAB spectral components, except for the artifact crystals formed especially in the lower part of the field, are detectable in this sample, yet, spectral components of both hematoxylin and Fast Red are readily detectable.

Figure 11A:
Figure 11B:
Figure 11C:
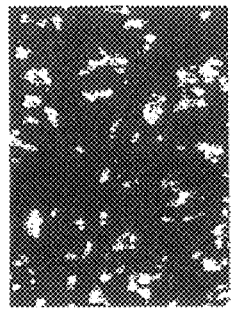
Figure 11D:
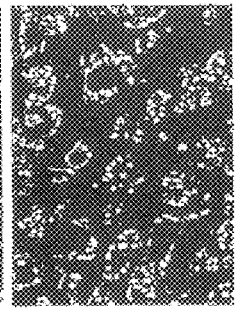
Figure 11E:

FIGS. 11a–e show images of a breast cancer sample which was previously and independently determined to be ER(+)/PR(+). The sample was co-stained with the histological stain hematoxylin and with the immunohistochemical stains anti-ER-DAB and anti-PR-Fast Red. FIG. 11a presents an RGB image of the sample. FIGS. 11b–d present binarized images of hematoxylin, DAB and Fast Red spectral components, respectively. FIG. 11e presents a classification overlay image, wherein the above spectral components are highlighted in red, green and blue, respectively. Regions co-stained with anti-ER-DAB and anti-PR-Fast Red are shown in yellow. Please note that as expected hematoxylin, DAB, as well as Fast Red spectral components are readily detectable.

FIGS. 12a–f show images of a breast cancer sample which was previously and independently determined to be ER(+)/PR(+). The sample was co-stained with the histological stains hematoxylin and eosin and with the immunohistochemical stains anti-ER-DAB and anti-PR-Fast Red. FIG. 12a presents an RGB image of the sample. FIGS. 12b–e present binarized images of hematoxylin, eosin, DAB and Fast Red spectral components, respectively. FIG. 12f presents a classification overlay image, wherein the above spectral components are highlighted in blue, purple green and red, respectively, showing the ability of the SPECTRACUBE™ system to resolve four different spectral components. Thus, this example shows a stained breast cancer tissue section simultaneously showing staining to nuclei (hematoxylin), cytoplasm (eosin), estrogen receptor (ER, detected with anti-ER/HRP/DAB), and progesterone receptor (PR, detected with anti-PR/HRP/DAB). In the images show some ER(+) cells and fewer PR(+) cells. Different areas on entire slide represent interductal (ER(+)/PR(+)) and intraductal (ER(+)/PR(−)) carcinoma. This image shows a duct, so mostly ER(+)/PR(−) cancer cells were expected.

Figure 13:
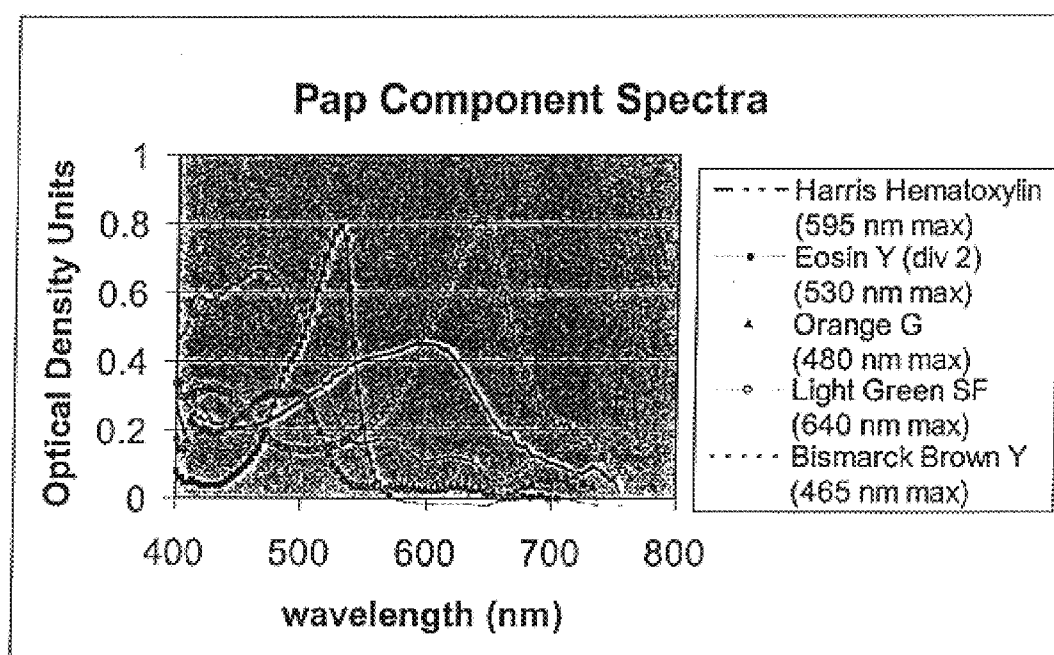
FIG. 13 presents non-normalized spectra of five histological stains (Harris hematoxylin, eosin, orange G, light green SF and Bismark brown Y) measured using the SPECTRACUBE™ system from five single stain stained cervix cancer samples. Peak wavelengths are indicated on the right.

FIG. 13 presents non-normalized spectra of five histological stains (Harris hematoxylin, eosin, orange G, light green SF and Bismark brown Y) measured using the SPECTRACUBE™ system from five single stain stained cervix cancer samples. Peak wavelengths are indicated on the right.

Figure 14B:
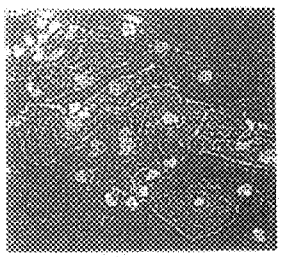
Figure 14C:
Figure 14D:
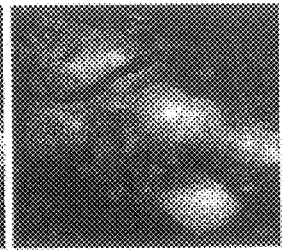
Figure 14E:
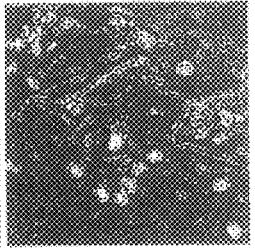
Figure 14A:
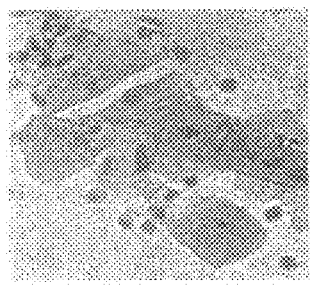
Figure 14G:
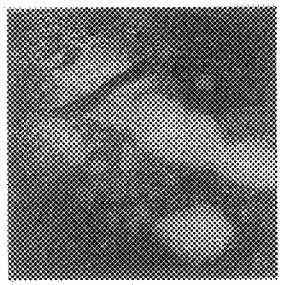
Figure 14F:
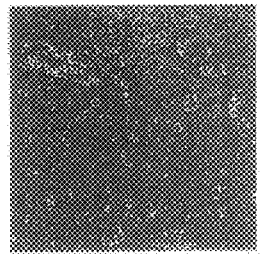

FIGS. 14a–g show images of a cervix cancer sample co-stained with the histological stains Harris hematoxylin, eosin, orange G, light green SF and Bismark brown Y, which collectively form what is known in the art as Papanicolaou (Pap) stain. FIG. 14a presents an RGB image of the sample. FIGS. 14b–f present binarized images of Harris hematoxylin, eosin, orange G, light green SF and Bismark brown Y spectral components, respectively. FIG. 14e presents a classification overlay image, wherein the above spectral components are highlighted in blue, pink, orange, green and gray, respectively, to form by combinations thereof the colorful classification overlay image shown. Please note that each of the stains employed has a unique staining pattern which could be resolved only due to the high spectral and spatial resolutions of the SPECTRACUBE™ system employed.

The data presented herein demonstrates the usefulness of a device having high spectral and spatial resolutions in the analysis of biological samples co-stained with multiple stains.

It will be appreciated by one ordinarily skilled in the art that the algorithms and displays used under this example, can be replaced by numerous other algorithms and displays, one example being the linear decomposition algorithm described in U.S. patent Ser. No. 08/984,990, which is incorporated by reference as if fully set forth herein. Using this algorithm will enable a researcher to obtain otherwise very similar and indicative results.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of in situ analysis of a biological sample comprising the steps of:

(a) staining the biological sample with N stains of which a first stain is selected from the group consisting of a first immunohistochemical stain, a first histological stain and a first DNA ploidy stain, and a second stain is selected from the group consisting of a second immunohistochemical stain, a second histological stain and a second DNA ploidy stain, with provisions that N is an integer greater than three and further that:

(i) if said first stain is said first immunohistochemical stain then said second stain is either said second histological stain or said second DNA ploidy stain;

(ii) if said first stain is said first histological stain then said second stain is either said second immunohistochemical stain or said second DNA ploidy stain; whereas (iii) if said first stain is said first DNA ploidy stain then said second stain is either said second immunohistochemical stain or said second histological stain; and (b) using a spectral data collection device for collecting spectral data from said biological sample, said spectral data collection device and said N stains are selected such that a spectral component associated with each of said N stains is collectable.

2. The method of claim 1, wherein said spectral data collection device is selected from the group consisting of an interferometer-based spectral data collection device, filters-based spectral data collection device and a dispersion element-based spectral data collection device.

3. The method of claim 1, wherein said first and second immunohistochemical stains each independently includes a primary antibody.

4. The method of claim 3, wherein said primary antibody is selected from the group consisting of anti-estrogen receptor antibody, anti-progesterone receptor antibody, anti-p53 antibody, anti-Her-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

5. The method of claim 3, wherein said primary antibody is labeled with a detectable moiety.

6. The method of claim 5, wherein said detectable moiety is a fluorescent dye.

7. The method of claim 6, wherein said fluorescent dye is selected from the group consisting of Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1, 3-diazol-4-yl)amino] caproyl] (NBD), BODIPY™, boron dipyrromethene difluoride, Oregon Green, MITOTRACKER™ Red, DiOC$_7$ (3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

8. The method of claim 5, wherein said detectable moiety is a non-fluorescent dye.

9. The method of claim 8, wherein said non-fluorescent dye includes a heavy metal.

10. The method of claim 5, wherein said detectable moiety is an enzyme catalyzing a colorimetric reaction of a substrate having a substantially non-soluble color reaction product.

11. The method of claim 10, wherein said enzyme is selected from the group consisting of alkaline phosphatase, horseradish peroxidase, β-galactosidase, and glucose oxidase.

12. The method of claim 10, wherein said substrate is selected from the group consisting of alkaline phosphatase substrates, horseradish peroxidase substrates, glucose oxidase substrates and beta-galactosidase substrates.

13. The method of claim 5, wherein said detectable moiety is an enzyme catalyzing a luminescence reaction of a substrate having a substantially non-soluble reaction product capable of luminescencing or of chemical involvement in a second reaction with at least one additional substrate, said second reaction having a luminescencing product.

14. The method of claim 13, wherein said enzyme is selected from the group consisting of alkaline phosphatase, horseradish peroxidase, β-galactosidase and glucose oxidase.

15. The method of claim 13, wherein said first and at least one additional substrates are each independently selected from the group consisting of alkaline phosphatase, horseradish peroxidase, β-galactosidase and glucose oxidase substrates.

16. The method of claim 1, wherein said first and second immunohistochemical stains each independently includes a primary antibody and a signal amplification mechanism.

17. The method of claim 16, wherein said signal amplification mechanism is selected from the group consisting of a secondary antibody capable of binding a constant region of said primary antibody, avidin or strepavidin capable of binding biotin conjugated to said primary antibody and biotin capable of binding avidin or strepavidin conjugated to said primary antibody.

18. The method of claim 14, wherein said secondary antibody, avidin, strepavidin and biotin are each independently labeled with a detectable moiety.

19. The method of claim 18, wherein said detectable moiety is a fluorescent dye.

20. The method of claim 19, wherein said fluorescent dye is selected from the group consisting of Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1, 3-diazol-4-yl)amino] caproyl] (NBD), BODIPY™, boron dipyrromethene difluoride, Oregon Green, MITOTRACKER™ Red, DiOC$_7$ (3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

21. The method of claim 18, wherein said detectable moiety is a non-fluorescent dye.

22. The method of claim 21, wherein said non-fluorescent dye is selected from the group consisting of alkaline phosphatase, horseradish peroxidase, glucose oxidase and beta-galactosidase substrates.

23. The method of claim 18, wherein said detectable moiety is an enzyme catalyzing a colorimetric reaction of a substrate having a substantially non-soluble color reaction product.

24. The method of claim 23, wherein said enzyme is selected from the group consisting of alkaline phosphatase, horseradish peroxidase, β-galactosidase, and glucose oxidase.

25. The method of claim 23, wherein said substrate is selected from the group consisting of alkaline phosphatase, horseradish peroxidase, β-galactosidase, and glucose oxidase substrates.

26. The method of claim 18, wherein said detectable moiety is an enzyme catalyzing a luminescence reaction of a substrate having a substantially non-soluble reaction product capable of luminescencing or of directing a second reaction of a second substrate having a luminescencing product.

27. The method of claim 26, wherein said enzyme is selected from the group consisting of luciferase and aequorin.

28. The method of claim 26, wherein said first and second substrates are each independently selected from the group consisting of luciferine, ATP, coelenterazine and Ca$^{++}$.

29. The method of claim 1, wherein said first and second histological stains are each independently selected from the group consisting of 4',6-diamidino-2-phenylindole, Eosin, Fluorescein isothiocyanate, Hoechst 33258, Hoechst 33342, Propidium Iodide, Quinacrine, Fluorescein-phalloidin, Resorufin, hematoxylin, Orange G, Light Green SF, Romanowsky-Giemsa, May-Grunwald, Blue counterstain, ethyl green, Feulgen-naphthol yellow S, Giemsa, Methylene Blue, Methyl Green, pyronin, Naphthol-yellow, Neutral Red, Papanicolaou stain, Red Counterstain C and Sirius Red.

30. The method of claim 1, wherein said first and second DNA ploidy stains are each independently selected from the group consisting of Chromomycin A 3, DAPI, Acriflavine-Feulgen reaction, Auramine O-Feulgen reaction, Ethidium Bromide, Propidium iodide, high affinity DNA fluorophores, Green Fluorescent Protein fused to DNA binding protein, ACMA, Quinacrine and Acridine Orange, Feulgen reagent, Gallocyanin chrom-alum, Gallocyanin chrom-alum and naphthol yellow S, Methyl green-pyronin Y and Thionin-Feulgen reagent.

31. A method of in situ analysis of a biological sample comprising the steps of:
(a) staining the biological sample with a plurality of stains of which a first stain is selected from the group consisting of a first immunohistochemical stain, a first histological stain and a first DNA ploidy stain, and a second stain is selected from the group consisting of a second immunohistochemical stain, a second histological stain and a second DNA ploidy stain, with a provision that:

(i) if said first stain is said first immunohistochemical stain then said second stain is either said second histological stain or said second DNA ploidy stain;

(ii) if said first stain is said first histological stain then said second stain is either said second immunohistochemical stain or said second DNA ploidy stain; whereas (iii) if said first stain is said first DNA ploidy stain then said second stain is either said second immunohistochemical stain or said second histological stain; and (b) using a spectral data collection device for collecting spectral data from said biological sample, said spectral data collection device and said plurality of stains are selected such that a spectral component associated with each of said plurality of stains is collectable.

32. The method of claim 31, wherein said spectral data collection device is selected from the group consisting of an interferometer-based spectral data collection device, filters-based spectral data collection device and a dispersion element-based spectral data collection device.

33. The method of claim 31, wherein said first and second immunohistochemical stains each independently includes a primary antibody.

34. The method of claim 33, wherein said primary antibody is selected from the group consisting of anti-estrogen receptor antibody, anti-progesterone receptor antibody, anti-p53 antibody, anti-Her-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

35. The method of claim 33, wherein said primary antibody is labeled with a detectable moiety.

36. The method of claim 35, wherein said detectable moiety is a fluorescent dye.

37. The method of claim 36, wherein said fluorescent dye is selected from the group consisting of Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1, 3-diazol-4-yl)amino] caproyl] (NBD), BODIPY™, boron dipyrromethene difluoride, Oregon Green, MITOTRACKER™ Red, DiOC$_7$ (3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

38. The method of claim 35, wherein said detectable moiety is a non-fluorescent dye.

39. The method of claim 38, wherein said non-fluorescent dye includes a heavy metal.

40. The method of claim 35, wherein said detectable moiety is an enzyme catalyzing a colorimetric reaction of a substrate having a substantially non-soluble color reaction product.

41. The method of claim 40, wherein said enzyme is selected from the group consisting of alkaline phosphatase, horseradish peroxidase, β-galactosidase, and glucose oxidase.

42. The method of claim 40, wherein said substrate is selected from the group consisting of alkaline phosphatase substrates, horseradish peroxidase substrates, glucose oxidase substrates and beta-galactosidase substrates.

43. The method of claim 35, wherein said detectable moiety is an enzyme catalyzing a luminescence reaction of a substrate having a substantially non-soluble reaction product capable of luminescencing or of chemical involvement in a second reaction with at least one additional substrate, said second reaction having a luminescencing product.

44. The method of claim 43, wherein said enzyme is selected from the group consisting of alkaline phosphatase, horseradish peroxidase, β-galactosidase and glucose oxidase.

45. The method of claim 43, wherein said first and at least one additional substrates are each independently selected from the group consisting of alkaline phosphatase, horseradish peroxidase, β-galactosidase and glucose oxidase substrates.

46. The method of claim 31, wherein said first and second immunohistochemical stains each independently includes a primary antibody and a signal amplification mechanism.

47. The method of claim 46, wherein said signal amplification mechanism is selected from the group consisting of a secondary antibody capable of binding a constant region of said primary antibody, avidin or strepavidin capable of binding biotin conjugated to said primary antibody and biotin capable of binding avidin or strepavidin conjugated to said primary antibody.

48. The method of claim 44, wherein said secondary antibody, avidin, strepavidin and biotin are each independently labeled with a detectable moiety.

49. The method of claim 48, wherein said detectable moiety is a fluorescent dye.

50. The method of claim 49, wherein said fluorescent dye is selected from the group consisting of Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1, 3-diazol-4-yl)amino]

caproyl] (NBD), BODIPY™, boron dipyrromethene difluoride, Oregon Green, MITOTRACKER™ Red, $DiOC_7$(3), $DiIC_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

51. The method of claim 48, wherein said detectable moiety is a non-fluorescent dye.

52. The method of claim 51, wherein said non-fluorescent dye is selected from the group consisting of alkaline phosphatase, horseradish peroxidase, glucose oxidase and beta-galactosidase substrates.

53. The method of claim 48, wherein said detectable moiety is an enzyme catalyzing a colorimetric reaction of a substrate having a substantially non-soluble color reaction product.

54. The method of claim 53, wherein said enzyme is selected from the group consisting of alkaline phosphatase, horseradish peroxidase, β-galactosidase, and glucose oxidase.

55. The method of claim 53, wherein said substrate is selected from the group consisting of alkaline phosphatase, horseradish peroxidase, β-galactosidase, and glucose oxidase substrates.

56. The method of claim 48, wherein said detectable moiety is an enzyme catalyzing a luminescence reaction of a substrate having a substantially non-soluble reaction product capable of luminescencing or of directing a second reaction of a second substrate having a luminescencing product.

57. The method of claim 56, wherein said enzyme is selected from the group consisting of luciferase and aequorin.

58. The method of claim 56, wherein said first and second substrates are each independently selected from the group consisting of luciferine, ATP, coelenterazine and $Ca^{++}$.

59. The method of claim 31, wherein said first and second histological stains are each independently selected from the group consisting of 4',6-diamidino-2-phenylindole, Eosin, Fluorescein isothiocyanate, Hoechst 33258, Hoechst 33342, Propidium Iodide, Quinacrine, Fluorescein-phalloidin, Resorufin, hematoxylin, Orange G, Light Green SF, Romanowsky-Giemsa, May-Grunwald, Blue counterstain, ethyl green, Feulgen-naphthol yellow S, Giemsa, Methylene Blue, Methyl Green, pyronin, Naphthol-yellow, Neutral Red, Papanicolaou stain, Red Counterstain C and Sirius Red.

60. A method of in situ analysis of a biological sample comprising the steps of:
   (a) staining the biological sample with at least four different immunohistochemical stains; and
   (b) using a spectral data collection device for collecting spectral data from said biological sample, said spectral data collection device and said at least four immunohistochemical stains are selected such that a spectral component associated with each of said at least four immunohistochemical stains is collectable.

61. The method of in situ analysis of a biological sample comprising the steps of:
   (a) staining the biological sample with at least three stains of which at least one stain is an immunohistochemical stain and at least one additional stain is a histological stain or a DNA ploidy stain; and
   (b) using a spectral data collection device for collecting spectral data from said biological sample, said spectral data collection device and said at least three stains are selected such that a spectral component associated with each of said at least three stains is collectable.

62. A method of in situ analysis of a biological sample comprising the steps of:
   (a) staining the biological sample with at least three stains of which a first stain is an immunohistochemical stain, a second stain is a histological stain and a third stain is a DNA ploidy stain; and
   (b) using a spectral data collection device for collecting spectral data from said biological sample, said spectral data collection device and said at least three stains are selected such that a spectral component specifically associated with each of said at least three stains is collectable.

63. An immunohistochemical composition comprising at least four different immunohistochemical stains, each being for staining a respective cytological marker and each being individually detectable in a presence of all others using a spectral data collection device.

* * * * *